US007063850B1

(12) United States Patent
Dale

(10) Patent No.: US 7,063,850 B1
(45) Date of Patent: Jun. 20, 2006

(54) PROTECTIVE ANTIGEN OF GROUP A STREPTOCOCCI

(75) Inventor: James B. Dale, Memphis, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

(21) Appl. No.: 09/471,817

(22) Filed: Dec. 22, 1999

Related U.S. Application Data

(60) Provisional application No. 60/114,730, filed on Dec. 31, 1998, provisional application No. 60/113,794, filed on Dec. 22, 1998.

(51) Int. Cl.
| A61K 39/02 | (2006.01) |
| A61K 39/09 | (2006.01) |
| A61K 39/38 | (2006.01) |
| A61K 38/00 | (2006.01) |
| C07K 1/00  | (2006.01) |

(52) U.S. Cl. .............................. 424/190.1; 424/234.1; 424/244.1; 424/184.1; 530/350; 530/825; 530/300; 514/2

(58) Field of Classification Search ................ 530/350, 530/300, 825; 424/184.1, 244.1, 234.1, 190.1; 514/2
See application file for complete search history.

(56) References Cited

U.S. PATENT DOCUMENTS

| 4,399,216 A | 8/1983 | Axel et al. ...................... 435/6 |
| 4,411,993 A | 10/1983 | Gillis ........................... 435/68 |
| 4,543,439 A | 9/1985 | Frackelton, Jr. et al. ...... 935/92 |
| RE32,011 E | 10/1985 | Zimmerman et al. ... 260/112 B |
| 4,579,821 A | 4/1986 | Palmiter et al. ......... 435/172.3 |
| 4,704,362 A | 11/1987 | Itakura et al. .............. 435/253 |
| 4,766,075 A | 8/1988 | Goeddel et al. ......... 435/240.2 |
| 4,784,950 A | 11/1988 | Hagen et al. .................. 435/68 |
| 4,801,542 A | 1/1989 | Murray et al. ........... 435/172.3 |
| 4,902,614 A | 2/1990 | Wakabayashi et al. ......... 435/7 |
| 4,935,349 A | 6/1990 | McKnight et al. ......... 435/69.5 |
| 4,987,071 A | 1/1991 | Cech et al. .................... 435/91 |
| 5,132,405 A | 7/1992 | Huston et al. ........... 530/387.3 |
| 5,219,740 A | 6/1993 | Miller et al. ............... 435/69.6 |
| 5,254,678 A | 10/1993 | Haseloff et al. ........... 536/23.2 |
| 5,359,051 A | 10/1994 | Cook et al. ................ 536/26.7 |
| 5,443,439 A | 8/1995 | Ohshita ........................ 601/90 |
| 5,686,272 A | 11/1997 | Marshall et al. ........... 435/91.2 |
| 5,843,454 A * | 12/1998 | Devico et al. ......... 424/196.11 |
| 6,100,380 A * | 8/2000 | Green et al. ................ 530/328 |
| 6,156,337 A * | 12/2000 | Barenholz et al. .......... 424/450 |
| 6,436,391 B1 * | 8/2002 | Foster et al. ............... 424/85.7 |
| 6,630,617 B1 * | 10/2003 | Famodu et al. ............. 800/298 |

FOREIGN PATENT DOCUMENTS

| EP | 415 731 A2 | 3/1991 |
| EP | 612 844 A2 | 8/1994 |
| EP | 360 257 B1 | 11/1996 |
| WO | WO 90/07936 | 7/1990 |
| WO | WO 91/02805 | 3/1991 |
| WO | WO 92/06693 | 4/1992 |
| WO | WO 93/10218 | 5/1993 |
| WO | WO 93/11230 | 6/1993 |
| WO | WO 93/25234 | 12/1993 |
| WO | WO 93/25698 | 12/1993 |
| WO | WO 94/03622 | 2/1994 |
| WO | WO 94/06421 | 3/1994 |
| WO | WO 94/06465 | 3/1994 |
| WO | WO 94/26914 | 11/1994 |
| WO | WO 95/10607 | 4/1995 |
| WO | WO 98/01561 | 1/1998 |
| WO | WO 9801561 A1 * | 1/1998 |

OTHER PUBLICATIONS

Burgess et al. J. Cell Biol. 111: 2129-2138, 1990.*
Lazar et al. Mol. Cellular Biol. 8: 1247-1252, 1988.*
Bowie et al. Science 247: 1306-1310, 1990.*
McGuinnes et al. Mol. Microbiol. 7: 505-514, Feb. 1993.*
McGuinnes et al. Lancet 337: 514-517, Mar. 1991.*
Harlow et al. In: Antibodies: A Laboratory Manual. Cold Spring Harbor Laboratory. Chapter 5, p. 76, 1988.*
Rudinger J. In: Peptide Hormones. (Ed) JA Parsons. University Park Press, Jun. 1976.*
Houghten et al. Vaccines86, Cold Spring Harbor Laboratory, p. 21-25, 1986.*
Alber and Kawasaki, "Nucleotide Sequence of the Triose Phosphate Isomerase Gene of *Saccharomyces cerevisiae*," *Journal of Molecular and Applied Genetics* 1: 419-434, 1982.
Altschul, S., "Amino Acid Substitution Matrices from an Information Theoretic Perspective," *J. Mol. Biol.* 219: 555-565, 1991.
Ammerer, G., *Methods in Enzymology*, vol. 101, Academic Press, Inc., New York, Wu et al. (eds.), 1983, Chapter 11, "Expression of Genes in Yeast Using the ADCI Promoter," pp. 193-201.

(Continued)

*Primary Examiner*—S. Devi
(74) *Attorney, Agent, or Firm*—Seed Intellectual Property Law Group PLLC

(57) ABSTRACT

The present invention provides the discovery of a new *Streptococcus* protective antigen (herein designated Spa) which has been identified and isolated from Streptococci. Spa is a surface antigen distinct from M protein which evokes opsonic antibodies that are protective against multiple serotypes of streptococci. The invention further provides isolated Spa polypeptides, proteins, peptides, and antibodies against the same, as well as nucleic acids encoding Spa polypeptide and peptide antigens. Also provided are methods for identification and isolation of a Spa polypeptide, therapeutic compositions comprised of Spa antigens or antibodies and methods of their use in protecting an animal against a *Streptococcus* infection.

7 Claims, 8 Drawing Sheets

OTHER PUBLICATIONS

Atkinson et al., "Baculoviruses as Vectors for Foreign Gene Expression in Insect Cells," *Pestic. Sci. 28*: 215-224, 1990.

Beggs, J., "Transformation of yeast by a replicating hybrid plasmid," *Nature 275*: 104-108, Sep. 14, 1978.

Beggs et al., "Characterization of *Mycobacterium tuberculosis* Complex Direct Repeat Sequence for Use in Cycling Probe Reaction," *Journal of Clinical Microbiology 34*(12): 2985-2989, Dec. 1996.

Bekkaoui et al., "Cycling Probe Technology with Rnase H Attached to an Oligonucleotide," *BioTechniques 20*(2): 240-248, Feb. 1996.

Bergman et al., "Two regulatory elements for immunoglobulin κ light chain gene expression," *Proc. Natl. Acad. Sci. USA 81*: 7041-7045, Nov. 1984.

Bird et al., "Single-Chain Antigen-Binding Proteins," *Science 242*: 423-426, Oct. 21, 1988.

Bolivar et al., "Construction And Characterization Of New Cloning Vehicles II. A Multipurpose Cloning System," *Gene 2*: 95-113, 1977.

Boshart et al., A Very Strong Enhancer Is Located Upstream of an Immediate Early Gene of Human Cytomegalovirus, *Cell 41*: 521-530, Jun. 1985.

Botstein et al., "Sterile Host Yeasts (SHY): A Eukaryotic System Of Biological Containment For Recombinant DNA Experiments," *Gene 8*: 17-24, 1979.

Broach et al., "Transformation In Yeast: Development Of a Hybrid Cloning Vector And Isolation Of The *CAN1* Gene," *Gene 8*: 121-133, 1979.

Chadwick et al., "A sensitive and robust method for measles RNA detection," *Journal of Virological Methods 70*: 59-70, 1998.

Chang et al., "Phenotypic expression in *E. coli* of a DNA sequence coding for mouse dihydrofolate reductase," *Nature 275*: 617-624, Oct. 19, 1978.

Chappell and Stuart, "Demonstration of protection in mice from a lethal challenge of three M serotypes of *Streptococcus pyogenes* using an M-negative vaccine," *Vaccine 11*(6): 643-648, 1993.

Chaudhary et al., "A recombinant immunotoxin consisting of two antibody variable domains fused to *Pseudomonas exotoxin*," *Nature 339*:394-397, Jun. 1, 1989.

Cook and Self, *Monoclonal Antibodies: Production, Engineering, and Clinical Application*, Ritter and Ladyman (eds.), Cambridge University Press, 1995, Chapter 9, "Monoclonal antibodies in diagnostic immunoassays," pp. 180-208.

Czakó and Márton, "The Herpes Simplex Virus Thymidine Kinase Gene as a Conditional Negative-Selection Marker Gene in *Arabidopsis thaliana*," *Plant Physiol. 104*: 1067-1071, 1994.

Dale et al., "New protective antigen of group A streptococci," *The Journal of Clinical Investigation 103*(9): 1261-1268, May 1999.

DeNoto et al., "Human growth hormone DNA sequence and mRNA structure: possible alternative splicing," *Nucleic Acids Research 9*(15): 3719-3730, 1981.

Dyer et al., "Quantitation of human immunodeficiency virus tpe 1 RNA in cell free seminal plasma: comparison of NASBA™ with Amplicor™ reverse transcription-PCR amplification and correlation with quantitative culture," *Journal of Virological Methods 60*: 161-170, 1996.

Ehricht et al., "Cooperative amplification of templates by cross-hybridization (CATCH)," *Eur. J. Biochem. 243*: 358-364, 1997.

Elvin et al., "Modified bacteriophage lambda promoter vectors for overproduction of proteins in *Escherichia coli*," *Gene 87*: 123-126, 1990.

Graham et al., "Characteristics of a Human Cell Line Transformed by DNA from Human Adenovirus Type 5," *J. Gen. Virol. 36*: 59-72, 1977.

Grant et al., "Improved RNA sequencing method to determine immunoglobulin mRNA sequence," *Nucleic Acids Research 15*(13): 5496, 1987.

Henikoff and Henikoff, "Amino acid substitution matrices from protein blocks," *Proc. Natl. Acad. Sci. USA 89*: 10915-10919, Nov. 1992.

Hinnen et al., "Transformation of yeast," *Proc. Natl. Acad. Sci. USA 75*(4): 1929-1933, Apr. 1978.

Hitzeman et al., "Isolation and Characterization of the Yeast 3-Phosphoglycerokinase Gene (PGK) by an Immunological Screening Technique," *The Journal of Biological Chemistry 255*(24): 12073-12080, Dec. 25, 1980.

Koering et al., "Induced Expression of the Conditionally Cytotoxic Herpes Simplex Virus *thymidine kinase* Gene by Means of a Parvoviral Regulatory Circuit," *Human Gene Therapy 5*: 457-463, 1994.

Larrick et al., "Polymerase Chain Reaction Using Mixed Primers: Cloning Of Human Monoclonal Antibody Variable Region Genes From Single Hybridoma Cells," *BioTechnology 7*: 934-938, Sep. 1989.

Loh et al., "Molecular Basis of a Mouse Strain-Specific Anti-Hapten Response," *Cell 33*: 85-93, May 1983.

McKnight et al., "Identification and molecular analysis of a third *Aspergillus nidulans* alcohol dehydrogenase gene," *The EMBO Journal 4*(6): 2093-2099, 1983.

Meehan et al., "Affinity purification and characterization of a fibrinogen-binding protein complex which protects mice against lethal challenge with *Streptococcus equi* subsp. *Equi*," *Microbiology 144*: 993-1003, 1998.

Messing, J., *Methods in Enzymology*, vol. 101, Wu et al. (eds.), Academic Press, Inc., 1983, vol. 101, "New M13 Vectors for Cloning," pp. 20-79.

Nichols and Yanofsky, *Methods in Enzymology*, vol. 101, Wu et al. (eds.), Academic Press, Inc., 1983, "Plasmids Contaning the *trp* Promoters of *Escherichia coli* and *Serratia marcescens* and Their Use in Expressing Cloned Genes," pp. 155-164.

Ohno et al., "Gene Therapy for Vascular Smooth Muscle Cell Proliferation After Arterial Injury," *Science 265*: 781-784, Aug. 5, 1994.

Ørskov and Nielsen, "Truncated glucagon-like peptide-1 (proglucagon 78-107 amide), an intestinal insulin-releasing peptide, has specific receptors on rat insulinoma cells (RIN 5 AH)," *FEBS Letters 229*(1): 175-178, Feb. 1988.

Paszkowski et al., "Direct gene transfer to plants," *The EMBO Journal 3*(12): 2717-2722, 1984.

Perry, M.J., *Monoclonal Antibodies*: Principles and Applications, Birch and Lennox (eds.), Wiley-Liss, Inc., 1995, Chapter 2.2, "The Role of Monoclonal Antibodies in the Advancement of Immunoassay Technology," pp. 107-120.

Riechmann et al., "Reshaping human antibodies for therapy," *Nature 332*: 323-327, Mar. 24, 1988.

Roberts et al., "Generation of an antibody with enhanced affinity and specificity for its antigen by protein engineering," *Nature 328*: 731-734, Aug. 20, 1987.

Russell and Bennett, "Construction and analysis of in vivo activity of *E. coli* promoter hybrids and promoter mutants that alter the −35 to −10 spacing," *Gene 20*: 231-243, 1982.

Scatchard, G., "The Attractions of Proteins for Small Molecules and Ions," *Ann. N.Y. Acad. Sci. 51*:660-672, 1949.

Sinkar et al., "Molecular biology of Ri-plasmid—A review," *J. Biosci. 11*(1-4): 47-57, Mar. 1987.

Struhl et al., "High-frequency transformation of yeast: Autonomous replication of hybrid DNA molecules," *Proc. Natl. Acad. Sci. USA 76*(3): 1035-1039, Mar. 1979.

Studier et al., "Use of T7 RNA Polymerase to Direct Expression of Cloned Genes," *Methods in Enzymology 185*: 60-89, 1990.

Subramani et al., "Expression of the Mouse Diydrofolate Reductase Complementary Deoxyribonucleic Acid in Simian Virus 40 Vectors," *Molecular and Cellular Biology 1*(2): 854-864, 1981.

Verhoeyen et al., "Reshaping Human Antibodies: Grafting an Antilysozyme Activity," *Science 239*: 1534-1536, Mar. 25, 1988.

Vieira and Messing, "The pUC plasmids, an M13mp7-derived system for insertion mutagenesis and sequencing with synthetic universal primers," *Gene 19*: 259-268, 1982.

Wu et al. (eds.), *Methods in Gene Biotechnology*, Boca Raton: CRC Press, 1997, Chapter 10, "Analysis of Gene Expression at the RNA Level," pp. 225-239.

Wu et al. (eds.), *Methods in Gene Biotechnology*, Boca Raton: CRC Press, 1997, Chapter 2, "Rapid Isolation of Specific cDNA's or Genes by PCR," pp. 15-28.

Young et al., *Genetic Engineering of Microorganisms for Chemicals*, Hollaender et al. (eds.), Plenum Press, New York and London, 1982, "The Alcohol Dehydrogenase Genes of the Yeast, *Saccharomyces cerevisiae*: Isolation, Stucture, and Regulation," pp. 335-361.

\* cited by examiner

| | |
|---|---|
| GAA GTG GCG GAC CCC TCT GAT AGT AAG AAA CTT ATT GAG TTA GGT TTG<br>Glu Val Ala Asp Pro Ser Asp Ser Lys Lys Leu Ile Glu Leu Gly Leu<br>1                    5                    10                 15 | 48 |
| GCT AAA TAC CTT AAT GAT AAA TTA CCC TTT AAA ACT AAA GAA GAT TCA<br>Ala Lys Tyr Leu Asn Asp Lys Leu Pro Phe Lys Thr Lys Glu Asp Ser<br>                20                  25                30 | 96 |
| GAG ATT TTA TCA GAG TTA CGT GAT GTA TTA AAA AAT GCT AAT CCA GAA<br>Glu Ile Leu Ser Glu Leu Arg Asp Val Leu Lys Asn Ala Asn Pro Glu<br>              35                  40                45 | 144 |
| ACA TTA AAA AGT TTA CTT AAT GGT ATG GAT CAA GGA CAT ATA TCA TTT<br>Thr Leu Lys Ser Leu Leu Asn Gly Met Asp Gln Gly His Ile Ser Phe<br>    50                  55                  60 | 192 |
| TCT GAT AGA AAT AAT CGC TAC AAC CGT TTA TCT CAA TAT ATA AAT AGT<br>Ser Asp Arg Asn Asn Arg Tyr Asn Arg Leu Ser Gln Tyr Ile Asn Ser<br>65                  70                  75                80 | 240 |
| TTT AGA AAA GAT GAT GAT GAC TAT CTA CAT AAT GGA TAT TCT TTA NGA<br>Phe Arg Lys Asp Asp Asp Asp Tyr Leu His Asn Gly Tyr Ser Leu Xaa<br>              85                  90                95 | 288 |
| AGT TTA GTG ATT GAA GCA ATT AAA TAC CGT TTA GAT AGC GAA TCC CAT<br>Ser Leu Val Ile Glu Ala Ile Lys Tyr Arg Leu Asp Ser Glu Ser His<br>            100                105              110 | 336 |

*Fig. 4*

```
        10          20          30          40
    *    *    *    *    *    *    *    *    *
ATA ATA TAC ATT CTT TCT TAT TAA ATA AAA ATA ACA ATG TAC TAC ATA
50           60          70          80          90
 *    *    *    *    *    *    *    *    *    *
AAG AAG TTT CTG CCA TTA AAA TAA AAG CAC CAT GAG ACT ATA ATA GTA
    100         110         120         130         140
     *    *    *    *    *    *    *    *    *
TGG TAA AAC AAA AAA GTA TGC CCA TAA CGG GTA GAG AGG AAT TGA CAT
     150         160         170         180         190
 *    *    *    *    *    *    *    *    *    *
ATG TTT TTG AGA AAT AAA AAG CAA AAA TTT AGC ATC AGA AAA CTA AGT
         200         210         220         230         240
 *    *    *    *    *    *    *    *    *    *
GCT GGT GCA GCA TCA GTA TTA GTT GCA GCA AGT GTG TTG GGA GGG GGA
             250         260         270         280
     *    *    *    *    *    *    *    *    *
GTA AGT GCG TAT GCA GAT TCA GTA AGT GGA TTA GAG GTG GCA GAC CCC
290         300         310         320         330
 *    *    *    *    *    *    *    *    *    *
TCT GAT AGT AAG AAA CTT ATT GAA TTA GGT TTG GCT AAA TAC CTT AAT
    340         350         360         370         380
     *    *    *    *    *    *    *    *    *
GAT AAA TTA CCC TTT AAA ACT AAA GAA GAT TCA GAG ATT TTA TCA GAG
         390         400         410         420         430
 *    *    *    *    *    *    *    *    *    *
TTA CGT GAT GTA TTA AAA AAT GCT AAT CCA GAA ACA TTA AAA AGT TTA
             440         450         460         470         480
 *    *    *    *    *    *    *    *    *    *
CTT AAT GGT ATG GAT CAA GGA CAT ATA TCA TTT TCT GAT AGA AAT AAT
             490         500         510         520
     *    *    *    *    *    *    *    *    *
CGC TAC AAC CGT TTA TCT CAA TAT ATA AAT AGT TTT AGA AAA GAT GAT
530         540         550         560         570
 *    *    *    *    *    *    *    *    *    *
GAT GAC TAT CTA CAT AAT GGA TAT TCT TTA GGA AGT TTA GTG ATT GAA
```

*Fig. 5A*

```
       580         590         600         610         620
        *     *     *     *     *     *     *     *     *
    GCA ATT AAA TAC CGT TTA GAT AGT GAG TCA CAT CTA AAG GAA GAA TTA
           630         640         650         660         670
        *     *     *     *     *     *     *     *     *     *
    CTT AAA CAG ACT GCA GAA CTT GAG CAA CGT AAG AAT GCA GAA GTT GAT
              680         690         700         710         720
        *     *     *     *     *     *     *     *     *     *
    TTA AAA TCT GAA AAA AAG AGA CTT GAA GCG CAA ATA NAA AAA GTA GGA
                 730         740         750         760
        *     *     *     *     *     *     *     *     *
    TAT GAT ATT GCT AAT AAA CAG CAA GAA TTA GAA AAA GCG CGT TCA GAT
    770         780         790         800         810
     *     *     *     *     *     *     *     *     *     *
    CAA AAA GAG TTA AGT GAA TCT ATT CAA AAA TTA ACG TCA CGA TTT AAA
       820         830         840         850         860
        *     *     *     *     *     *     *     *     *
    AAA GAA AGT GAT GCT AAA CAA AAA GAA CTA GAT GAA GCT AAG GCG GCA
           870         880         890         900         910
        *     *     *     *     *     *     *     *     *     *
    AAT AAA TCT CTT TCA GAG TCA GCA ACA AAA ACA TTA GCT AGA TCA TCT
              920         930         940         950         960
        *     *     *     *     *     *     *     *     *     *
    AAG ATA ACT AAT GAA TTA AAG GAT AAG TTG GCG GCT TCA GAA AAA GAT
                 970         980         990         1000
        *     *     *     *     *     *     *     *     *
    AAA AAT CGT GCA TTT CAA GTT TCT TCA GAG CTA GCT AAT AAG TTG CAT
    1010        1020        1030        1040        1050
     *     *     *     *     *     *     *     *     *     *
    GAA ACA GAA ACT AGT CGT GAT AAG GCT TTA GCA GAA TCA AAA GAA TTA
       1060        1070        1080        1090        1100
        *     *     *     *     *     *     *     *     *
    GCA GAT AAA TTG GCA GTT AAA ACA GCA GAA GCT GAA AAG TTA ATG GAA
           1110        1120        1130        1140        1150
        *     *     *     *     *     *     *     *     *     *
    AAC GTT GGT AGT CTA GAC CGC TTG GTA GAG TCT GCA AAA CGT GAA ATG
              1160        1170        1180        1190        1200
        *     *     *     *     *     *     *     *     *     *
    GCT CAA AAA TTA GCA GAA ATT GAC CAA TTA ACT GCT GAT AAG GCT AAG
                 1210        1220        1230        1240
        *     *     *     *     *     *     *     *     *
    GCT GAT GCA GAG CTT GCA GCT GCA AAT GAC ACC ATT GCA TCA CTT CAA
```

*Fig. 5B*

```
              1250        1260        1270        1280        1290
          *     *     *     *     *     *     *     *     *     *
         ACA GAG CTA GAA AAA GTT AAG ACA GAG CTT GCT GTT TCA GAG CGC TTG
             1300        1310        1320        1330        1340
          *     *     *     *     *     *     *     *     *
         ATC GAA TCA GGT AAA CGT GAA ATT GCT GAG CTT GAA AAA CAA AAA GAT
             1350        1360        1370        1380        1390
          *     *     *     *     *     *     *     *     *     *
         GCT TCT GAT AAG GCT TTA GCA GAA TCA CAA GCT AAT GTA GCA GAG CTT
                 1400        1410        1420        1430        1440
          *     *     *     *     *     *     *     *     *     *
         GAA AAA CAA AAA GCA GCA TCA GAT GCT AAG GTA GCA GAG CTT GAA AAA
                     1450        1460        1470        1480
          *     *     *     *     *     *     *     *     *
         GAA GTT GAA GCT GCT AAA GCT GAG GTT GCA GAT CTT AAA GCA CAA TTA
      1490        1500        1510        1520        1530
    *     *     *     *     *     *     *     *     *     *
         GCT AAG AAA GAA GAA GAG CTT GAA GCC GTT AAG AAA GAA AAA GAA GCG
             1540        1550        1560        1570        1580
          *     *     *     *     *     *     *     *     *
         CTT GAA GCT AAG ATT GAA GAG CTC AAA AAA GCT CAT GCT GAG GAA CTT
                 1590        1600        1610        1620        1630
          *     *     *     *     *     *     *     *     *     *
         TCA AAA CTT AAA GAA ATG CTT GAG AAG AAA GAC CAT GCG AAT GCA GAT
                     1640        1650        1660        1670        1680
          *     *     *     *     *     *     *     *     *     *
         CTT CAA GCA GAA ATC AAC CGC TTG AAG CAA GAG CTA GCT GAC AGG ATT
                 1690        1700        1710        1720
          *     *     *     *     *     *     *     *     *
         AAG TCA TTG TCA CAA GGT GGT CGT GCT TCA CAA ACA AAC CCA GGC TCT
      1730        1740        1750        1760        1770
    *     *     *     *     *     *     *     *     *     *
         ACA ACT GCT AAA GCA GGT CAA TTG CCA TCT ACT GGT GAG TCT GCT AAC
             1780        1790        1800        1810        1820
          *     *     *     *     *     *     *     *     *
         CCA TTC TTC ACT ATT GCA GCT CTT ACC GTC ATC GCT GGT GCT GGT ATG
                 1830        1840        1850        1860        1870
          *     *     *     *     *     *     *     *     *     *
         GCT GTG GTG TCT CCT AAA CGC AAA GAA AAC TAA GCT CTT TCC TCT TTC
```

*Fig. 5C*

Signal Peptide (1-37)                Mature Protein
MFLRNKKQKFSIRKLSAGAASVLVAASVLGGGVSAYADSVSGLEVADPSDSKKLIELGLAKYLN

DKLPFKTKEDSEILSELRDVLKNANPETLKSLLNGMDQGHISFSDRNNRYNRLSQYINSFRKDD

DDYLHNGYSLGSLVIEAIKYRLDSESHLKEELLKQTAELEQRKNAEVDLKSEKKRLEAQIXKVG

YDIANKQQELEKARSDQKELSESIQKLTSRFKKESDAKQKELDEAKAANKSLSESATKTLARSS

KITNELKDKLAASEKDKNRAFQVSSELANKLHETETSRDKALAESKELADKLAVKTAEAEKLME

NVGSLDRLVESAKREMAQKLAEIDQLTADKAKADAELAAANDTIASLQTELEKVKTELAVSERL

IESGKREIAELEKQKDASDKALAESQANVAELEKQKAASDAKVAELEKEVEAAKAEVADLKAQL

AKKEEELEAVKKEKEALEAKIEELKKAHAEELSKLKEMLEKKDHANADLQAEINRLKQELADRI

KSLSQGGRASQTNPGSTTAKAGQLPSTGESANPFFTIAALTVIAGAGMAVVSPKRKEN*

*Fig. 6*

PROTECTIVE ANTIGEN OF GROUP A STREPTOCOCCI

CROSS-REFERENCE TO RELATED APPLICATION

This application claims the benefit of U.S. Provisional Patent Application No. 60/114,730 filed Dec. 31, 1998; and U.S. Provisional Patent Application No. 60/113,794 filed Dec. 22, 1998. Both of these provisional applications are incorporated herein by reference in their entireties.

STATEMENT OF GOVERNMENT INTEREST

This invention was made with research funds from the Department of Veterans Affairs and the U.S. Public Health Service, National Institute of Allergy and Infectious Diseases under Grant No. AI-10085. The government may have certain rights in this invention.

TECHNICAL FIELD

The present invention relates to Streptococcal antigens, more particularly to polypeptide antigens and to nucleic acids encoding the same, which are useful for eliciting opsonic antibodies in an animal that are protective against infection by group A streptococci.

BACKGROUND OF THE INVENTION

Group A streptococcal infections cause a wide array of clinical syndromes, ranging from uncomplicated pharyngitis and pyoderma to serious, invasive infections and toxic shock syndrome. Protection against infection is largely mediated by antibodies against the surface M protein of the organisms. M protein is an alpha-helical, coiled-coil molecule that extends from the surface with its hypervariable N-terminus exposed to the outside and the conserved C-terminus buried in the cytoplasm. The N-terminus contains type-specific epitopes that evoke bactericidal antibodies that correlate with protection against the homologous serotype. The emm gene is located in a regulon that is controlled by the upstream positive regulator mga. Depending on the serotype, the regulon may contain one, two or three emm and emm-like genes. In serotypes containing only one emm gene, deletion or interruption of the emm gene results in an avirulent organism that can no longer resist phagocytosis. In serotypes that express several emm-like genes, each may partially contribute to resistance to phagocytosis, but among the many defined surface proteins of group A Streptococci, only antibodies against the M protein have been shown to be opsonic.

Understanding the molecular basis of non-M protein mediated cross serotype protection would aid in providing therapeutic treatments for a variety of infections cause by group A streptococci. Type 18 Streptococci have been identified as an important serotype in the resurgence of acute rheumatic fever in Utah. In addition, Types 3 and 18, and to a lesser extent Type 28 Streptococci have all been implicated in the recent resurgence of serious Streptococcal diseases. Each of these diseases could be potentially be prevented by vaccination with an antigen other than M protein, which is capable of eliciting a protective response across divergent serotypes.

Presently, there appears to be no showing in the art that group A streptococci (and all that follow-group A streptococci) express surface polypeptides or proteins containing opsonic epitopes not related to M protein. Providing polypeptides from Streptococci containing non-M protein antigens, especially those that have opsonic epitopes would enhance therapeutic tools available to protect against a variety of Streptococcal infections.

Therefore, there is a need in the art for the discovery and characterization of non-M protein antigens which are effective for protecting against such infections, especially antigens that are effective against multiple serotypes of group A Streptococci.

SUMMARY OF THE INVENTION

The present invention provides the discovery of a novel protective antigen isolated from a *Streptococcus* species that is distinct from M protein and that elicits opsonic antibodies that are effective against multiple serotypes of Streptococci. The novel antigen is a surface antigen of a group A Streptococci, which is herein designated as Spa (Streptococcal protective antigen).

In one aspect, the invention provides Spa polypeptides isolated from a *Streptococcus* species comprising a polypeptide having at least 50% amino acid sequence identity to SEQ. ID NO:2 or 5. In one embodiment, the Spa polypeptides are from a *streptococcus* which is a member of the species *Streptococcus pyogenes* (group A streptococci). Another embodiment includes an isolated Spa polypeptide from a group A, Type 18 Streptococci serotype. Still another embodiment is a Spa polypeptide comprising the amino acid sequence of SEQ. ID NOS: 2 or 5. Variants of this embodiment include amino acid sequences having conservative amino acid substitutions or those having at least 90% sequence identity to SEQ. ID NOS: 2 or 5.

In related embodiments, the invention provides any of the aforementioned isolated Spa polypeptides containing an opsonic epitope. In one embodiment, the isolated polypeptides contain an opsonic epitope comprised of contiguous amino acids from a portion of an N-terminus of the polypeptide that is exposed on an outside surface of a cell when the polypeptide is expressed in the cell. In another embodiment, the isolated Spa polypeptide contains an opsonic epitope comprised of at least 8 contiguous amino acids of the N-terminus of the polypeptide. In another embodiment, the isolated Spa polypeptide contains an opsonic epitope comprised of at least 23 contiguous amino acids of the N-terminus of the polypeptide of SEQ. ID NOS: 2 or 5 or polypeptides having at least 50% identity thereto. In still another embodiment, the isolated Spa polypeptide includes the peptide of SEQ. ID NO: 3 or variants thereof that contain an opsonic epitope.

In a second aspect, the invention provides an immunogen for protecting an animal against a *Streptococcus* infection where the immunogen is comprised of any of the aforementioned Spa polypeptides. One embodiment of this aspect provides an immunogen for protecting an animal against a *Streptococcus* infection comprising a peptide that includes at least 8 contiguous amino acids from an N terminus of the aforementioned Spa polypeptides. Another embodiment provides an immunogen comprised of a peptide that includes at least 23 contiguous amino acids from an N terminus of the Spa polypeptide of SEQ. ID NOS: 2 or 5 or polypeptides having at least 50% identity thereto. In another embodiment, the immunogen includes the peptide of SEQ. ID NO: 3 or variants thereof that contain an opsonic epitope. In other embodiments, the aforementioned immunogens are linked to a carrier protein or provided as a fusion protein. Another aspect of any of aforementioned immunogens are that they provides cross-protection against multiple serotypes of Streptococci. In one embodiment the immunogens provide protection against serotypes of Streptococci which are group A serotypes. In another embodiment, the serotypes are selected from Type 3, Type 18 and Type 28 Streptococci.

In a third aspect, this invention provide antibodies that specifically bind to an epitope present on the aforementioned Spa polypeptides. One embodiment includes antibodies that bind to an epitope comprised of at least 8 contiguous amino acids of the N-terminus of the Spa polypeptide. Another embodiment includes antibodies that bind to an epitope comprised of at least 23 contiguous amino acids of the N-terminus of the Spa polypeptide. In still another embodiment, the antibodies bind to a peptide according to SEQ. ID NO: 3 or variants thereof that contain an opsonic epitope. In still another embodiment, the invention provides the aforementioned antibodies which do not bind to an M protein of *Streptococcus* species.

In a fourth aspect, the invention provides an isolated nucleic acid molecule comprising a sequence that encodes the aforementioned *Streptococcus* Spa polypeptides or a complement of said nucleic acid molecule. In one embodiment, the isolated nucleic acid molecule is comprised of a sequence selected from SEQ. ID NOS: 1, or 4, or 5 a complement or variants thereof. Variants of the nucleic acid sequences include variants selected from sequences that encode the polypeptide of SEQ. ID NOS: 2 or 5 which are degenerate to SEQ. ID NOS: 1 or 4 because of the genetic code; sequences that encode a polypeptide which has conservative amino acid substitutions to the polypeptide of SEQ. ID NOS: 2 or 5, or sequences that encode a polypeptide that is at least 50% identical to SEQ. ID NOS: 2 or 5. In still another embodiment, the invention provides an isolated nucleic acid molecule comprising a sequence that hybridizes to the aforementioned nucleic acid molecules under conditions of moderate or high stringency. Another embodiment includes isolated nucleic acid molecules comprising a sequence that encodes an opsonic epitope form a Spa polypeptide comprising a polypeptide having at least 50% amino acid sequence identity to SEQ. ID NOS:2 or 5. A related aspect of the nucleic acid sequences provided herein include nucleic acid molecules encoding an opsonic epitope and further encoding a fusion polypeptide wherein the fusion polypeptide contains the opsonic epitope fused to at least one other peptide sequence. In one embodiment, the other peptide sequence includes a tag sequence that facilitates isolation of the fusion polypeptide from a cellular extract. In another embodiment, the other peptide sequence is a carrier protein.

A related embodiment to the aforementioned nucleic acid molecules includes a vector comprising those nucleic acid molecules operably linked to a promoter so that the vector expresses a polypeptide encoded by the isolated nucleic acid when the vector is introduced into a host cell. In another embodiment, the invention provides a host cell carrying such a vector.

A fifth aspect of this invention provides a therapeutic composition for protecting an animal from a *Streptococcus* infection comprising a biologically acceptable diluent and an effective amount of a an immunizing agent selected from the aforementioned polypeptides, peptides, immunogens, host cells and antibodies. In some embodiments, the therapeutic composition may include: a) a Spa polypeptide isolated from *Streptococcus*; b) an immunogen comprised of an opsonic epitope obtained from the Spa polypeptide; c) a host cell that expresses an opsonic epitope obtained from the Spa polypeptide; or d) an antibody that specifically binds to the Spa polypeptide. In another embodiment, the aforementioned immunizing agents may be conjugated to a polyvalent carrier.

A sixth related aspect of this invention includes a therapeutic method for protecting an animal against a *Streptococcus* infection comprising the step of administering to the animal the aforementioned therapeutic compositions wherein administering the therapeutic compositions elicits opsonic antibodies in the animal. In a preferred embodiment protection is provided against multiple serotypes of *Streptococcus*. In a related embodiment, the therapeutic composition is administered by at least one of oral administration, intranasal administration, parenteral (intramuscular, subcutaneous, or intravenous) vaccination. In another preferred embodiment, the therapeutic method is provided when the animal is a human.

In still another aspect, the present invention provides diagnostic compositions and methods for detecting infection by a *Streptococcus* species in a target sample. In one embodiment, primers derived from the nucleotide sequence of a Spa gene are used to amplify nucleic acids extracted from cells obtained from target sample. Typically, the extracted nucleic acid is DNA. Alternatively, the extracted nucleic acids contains mRNA. In one embodiment, diagnosis is performed by detecting a nucleic acid sequence amplified by PCR using primers provided in SEQ. ID NOS: 4 and 5. In other embodiments, primers are selected from any portion of a Spa gene or compliment thereof containing at least 12 contiguous nucleotides, wherein the primers specifically hybridize to a selected portion of the Spa gene. In still another embodiment, the invention provides probes useful in the diagnosis of a *Streptococcus* infection wherein the probes contain at least 12 contiguous nucleotides that specifically hybridize to a selected portion of the Spa gene.

In a different embodiments, the diagnostic compositions and methods of the present invention include antibodies that specifically bind to a Spa polypeptide. In one embodiment the antibodies are opsonic antibodies. In certain embodiments the antibodies are polyvalent antibodies while in other embodiments the antibodies are monoclonal antibodies. In still other embodiments, the antibodies are conjugated to a detectable signaling moiety. In other embodiments, the Spa antibodies are used in combination with other immunochemical reagents. In typical embodiments, the other immunochemical reagents form a complex with the Spa antibodies wherein the complex provides a detectable signal under conditions where a Spa polypeptide is bound to a Spa antibody.

In a related aspect, the invention provides diagnostic kits comprised of the aforementioned primers, probes or antibodies. In specific embodiments, the kits further contain reagents for detecting Spa nucleic acids which are amplified or which hybridize to the primers or probes provided herein. In another specific embodiment, the kits contain immunochemical reagents for detecting binding of Spa antibodies to Spa polypeptides isolated from a target sample.

These and other aspects of the present invention will become evident upon reference to the following detailed description and attached drawings. In addition, various references are set forth herein which describe in more detail certain procedures or compositions (e.g., plasmids, etc.), and are therefore incorporated by reference in their entirety.

BRIEF DESCRIPTION OF THE DRAWINGS

FIG. 4 shows a partial DNA sequence of an isolated spa gene and a deduced amino acid sequence for a Spa polypeptide. The sequence has been submitted to GenBank® and has the accession number AF086813.

FIG. 5 (presented in FIGS. 5A, 5B and 5C) shows a full length DNA sequence according to SEQ ID NO:4 encoding a Spa polypeptide. A start codon begins at position 145, a signal peptide is encoded by positions 145–255 and a mature protein begins at position 256.

FIG. 6 shows an amino acid sequence for a full length Spa polypeptide according to SEQ ID NO:5. A signal peptide at positions 1–3 is underlined.

DETAILED DESCRIPTION OF THE INVENTION

Definitions

Figure 1:
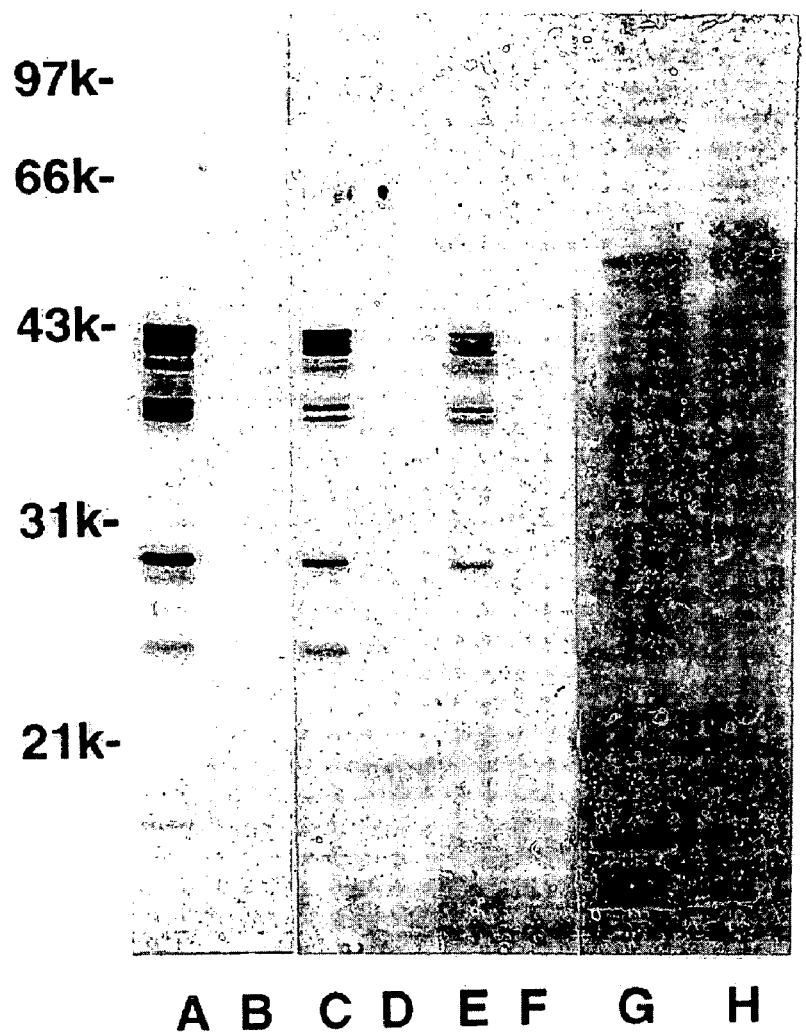
FIG. 1 depicts a Western blot analysis of whole-cell extracts of M18 (lanes A, C, and E) and M18Ω (lanes B, D, and F) reacted with rabbit antisera against rM18 (lanes A and B), SM18(1–30) (lanes C and D), and SM5(265–291) (lanes E and F). Coomassie® blue stained multiple proteins in extracts from both strains (M18, lane G and M18Ω, lane H).

Prior to setting forth the Invention in detail, it may be helpful to an understanding thereof to set forth definitions of certain terms and to list and to define the abbreviations that will be used hereinafter.

"Nucleic acid" or "nucleic acid molecule" refers to any of deoxyribonucleic acid (DNA), ribonucleic acid (RNA), oligonucleotides, fragments generated by the polymerase chain reaction (PCR), and fragments generated by any of ligation, scission, endonuclease action, and exonuclease action. Nucleic acids can be composed of monomers that are naturally-occurring nucleotides (such as deoxyribonucleotides and ribonucleotides), or analogs of naturally-occurring nucleotides (e.g., α-enantiomeric forms of naturally-occurring nucleotides), or a combination of both. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids," which comprise naturally-occurring or modified nucleic acid bases attached to a polyamide backbone. Nucleic acids can be either single stranded or double stranded.

An "isolated nucleic acid molecule" is a molecule that is not integrated in the genomic DNA of an organism. For example, a DNA molecule that encodes a Spa polypeptide that has been separated from the genomic DNA of a *Streptococcus* cell is an isolated DNA molecule. Another example of an isolated nucleic acid molecule is a chemically-synthesized nucleic acid molecule that is not integrated in the genome of an organism. The isolated nucleic acid molecule may be genomic DNA, cDNA, RNA, or composed at least in part of nucleic acid analogs.

An "isolated" polypeptide" is a polypeptide that has been removed by at least one step from its original environment. For example, a naturally occurring protein is isolated if it is separated from some or all of the coexisting material in the natural system such as carbohydrate, lipid, or other proteinaceous impurities associated with the polypeptide in nature. Within certain embodiments, a particular protein preparation contains an isolated polypeptide if it appears nominally as a single band on SDS-PAGE gel with Coomassie Blue staining.

" ""Promoter" is a nucleotide sequence that directs the transcription of a structural gene. Typically, a promoter is located in the 5' region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter.

"Vector" refers to an assembly which is capable of directing the expression of desired protein. The vector must include transcriptional promoter elements which are operably linked to the genes of interest. The vector may be composed of either deoxyribonucleic acids ("DNA"), ribonucleic acids ("RNA"), or a combination of the two (e.g., a DNA-RNA chimeric). Optionally, the vector may include a polyadenylation sequence, one or more restriction sites, as well as one or more selectable markers such as neomycin phosphotransferase or hygromycin phosphotransferase. Additionally, depending on the host cell chosen and the vector employed, other genetic elements such as an origin of replication, additional nucleic acid restriction sites, enhancers, sequences conferring inducibility of transcription, and selectable markers, may also be incorporated into the vectors described herein.

"Cloning vector" refers to nucleic acid molecules, such as a plasmid, cosmid, or bacteriophage, that has the capability of replicating autonomously in a host cell. Cloning vectors typically contain one or a small number of restriction endonuclease recognition sites at which foreign nucleotide sequences can be inserted in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

"Expression vector" refers to a nucleic acid molecule encoding a gene that is expressed in a host cell. Typically, gene expression is placed under the control of a promoter, and optionally, under the control of at least one regulatory element. Such a gene is said to be "operably linked to" the promoter. Similarly, a regulatory element and a promoter are operably linked if the regulatory element modulates the activity of the promoter.

"Recombinant host" refers to any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

"Moderate or stringent hybridization conditions" are conditions of hybridization of a probe nucleotide sequence to a target nucleotide sequence wherein hybridization will only be readily detectable when a portion of the target sequence is substantially similar to the complement of the probe sequence. Hybridization conditions vary with probe size as well as with temperature, time and salt concentration in a manner known to those of ordinary skill in the art. For example, moderate hybridization conditions for a 50 nucleotide probe would include hybridization overnight a buffer containing 5×SSPE (1×SSPE=180 mM sodium chloride, 10 mM sodium phosphate, 1 mM EDTA (pH 7.7), 5× Denhardt's solution (100× Denhardt's=2% (w/v) bovine serum albumin, 2% (w/v) Ficoll®, 2% (w/v) polyvinylpyrrolidone) and 0.5% SDS incubated overnight at 55–60° C. Post-hybridization washes at moderate stringency are typically performed in 0.5×SSC (1×SSC=150 mM sodium chloride, 15 mM trisodium citrate) or in 0.5×SSPE at 55–60° C. Stringent hybridization conditions typically would include 2×SSPE overnight at 42° C., in the presence of 50% formamide followed by one or more washes in 0.1–0.2×SSC and 0.1% SDS at 65° C. for 30 minutes or more.

"Percent identity" or "% identity" with reference to a subject polypeptide or peptide sequence is the percentage value returned by comparing the whole of the subject polypeptide sequence to a test sequence using a computer implemented algorithm, typically with default parameters. Sequence comparisons can be performed using any standard software program such as BLAST, tBLAST or MEGALIGN mentioned above Still others include those provided in the LASERGENE bioinformatics computing suite, which is produced by DNASTAR (Madison, Wis.). Reference for algorithms such as ALIGN or BLAST may be found for example, in Altschul, *J. Mol. Biol.* 219:555–565, 1991; Henikoff and Henikoff, *Proc. Natl. Acad. Sci. USA* 89:10915–10919, 1992) and BLAST® is available at the NCBI website www/ncbi.nlm.nih.gov/cgi-bin/BLAST.

Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in Methods in Gene Biotechnology, pages 123–151 (CRC Press, Inc. 1997), and Bishop (ed.), Guide to Human Genome Computing, 2nd Edition (Academic Press, Inc. 1998)).

"Spa" or "Spa polypeptide" should be understood to include any polypeptide, or nucleic acid encoding a polypeptide having at least 50%, 60%, 70%, 80%, 90%, or 95% amino acid identity to the polypeptides provided herein as SEQ ID NO:2, or 5.

"Specifically binds" means an antibody is able to selectively bind a peptide encoded by a spa gene of this invention. Such an antibody generally associates with a Spa polypeptide with an affinity constant ($K_a$) of at least $10^4$, preferably at least $10^5$, more preferably at least $10^6$, still more preferably at least $10^7$ and most preferably at least $10^8$. Affinity constants may be determined by one of ordinary skill in the art using well known techniques (see Scatchard, *Ann. N.Y. Acad. Sci.* 51:660–672, 1949).

Abbreviations: YAC, yeast artificial chromosome; PCR, polymerase chain reaction; RT-PCR, PCR process in which RNA is first transcribed into DNA at the first step using reverse transcriptase (RT); cDNA, any DNTA made by copying an RNA sequence into DNA form.

This invention provides a novel family of polypeptides isolated from a Streptococci species that are distinct from M protein and which provide antigens that elicit opsonic antibodies in an animal. These novel polypeptides, herein designated as Spa (Streptococcal protective antigens), contain opsonic epitopes that cross react with multiple serotypes of Streptococci. Also provided are nucleic acid molecules (SEQ ID NOS: 1 and 4) which encode representative Spa polypeptides (SEQ ID NOS: 2 and 5). SEQ ID NO:2 encodes a 112 residue polypeptide that is a part of the N-terminus of a mature Spa polypeptide. Also provided is a 23 amino acid peptide sequence (SEQ ID NO: 3) comprising a portion of an N-terminus of a Spa polypeptide which contains an opsonic epitope. The polypeptides of SEQ ID NOS: 2 and 3 are therefore part of a larger protein of about 50 kD encoded by a *Streptococcus* gene herein designated as spa. SEQ ID NO:4 is a full-length spa gene encoding the full-length pro-protein of SEQ ID NO:5. SEQ ID NOS: 2 and 3 are part of the mature protein and corresponds to position 44 of SEQ ID NO:5. The invention also encompasses variants of the nucleic acid represented by SEQ ID NOS: 1 and 4, and the polypeptides represented by SEQ ID NOS: 2, 3 or 5 which are further described hereafter. Vectors and host cells carrying nucleic acids encoding Spa or opsonic epitopes of Spa are also provided by the present invention.

The invention further includes immunogens comprised of Spa polypeptides and/or peptides comprised of contiguous amino acids from the N-terminus of a Spa polypeptide. Also included in this invention are antibodies that specifically bind to a Spa polypeptide or to antigens contained therein. The polypeptides, antigens, host cells expressing opsonic epitopes and antibodies that specifically bind thereto can each serve as immunizing agents in therapeutic compositions for protecting an animal from infection by multiple serotypes of Streptococci. Accordingly, this invention further encompasses such therapeutic compositions and methods of their use to protect an animal against a *Streptococcus* infection.

I. Polypeptides

The identification of the novel polypeptide from Streptococci was facilitated by production of an M-negative mutant of a Streptococcal strain that is fully virulent when compared to the parent strain. Production of a fully virulent M-negative mutant is a surprising result in light of prior teaching, such as provided for example by Moses, et al. who showed that an M-negative mutant of an M18 strain (87–282) had reduced virulence relative to the parent. The present invention demonstrates that production of an M-negative mutant provides a Streptococcal strain that maintains virulence and which exposes the presence of a non-M polypeptide displaying an opsonic epitope of a surface protein. As used herein, an "opsonic epitope" is that peptide or polypeptide portion of a protein which forms an antigen that elicits the production of, and binds to, opsonic antibodies evoked by immunizing an animal with a host cell containing the antigen. A "surface protein" is protein having a portion of its amino acid sequence displayed on the outer surface of a host cell which contains the protein. "Opsonic antibodies" has the meaning commonly understood by those of ordinary skill in the art as antibodies which facilitates phagocytic activity against a particle, such as a host cell, that contains the antigen.

One way to produce an M-negative mutant is by inactivation of an emm gene encoding an M protein in a Streptococcal strain. Suitable strains include any pathogenic Streptococci. In one embodiment of this invention, a group A Type 18 *Streptococcus* (designated M18) is used. Many methods are known in the art for inactivation of a bacterial gene are suitable for the practice of this invention. In one method exemplified herein, a Ω interposon element is introduced into the chromosome of a Streptococcal species to inactivate an emm gene present in a Type 18 *Streptococcus* serotype (emm18). One way to accomplished this is to first ligate a Ω interposon element into the coding sequence of an emm18 gene that has been cloned into a first vector so as to obtain a second vector containing an emm18 which is inactivated by insertion of the Ω element. This second vector is then used to transform a parent strain so that the inactivated emm18 recombines with and replaces the native emm18 gene present on the chromosome of the parent strain.

Insertionally inactivated strains can be screened for the presence of the inactivated emm18 gene by southern blotting using the Ω interposon element as a probe in combination with a probe for the emm18 gene. Inactivation of the emm18 gene can be confirmed by showing absence of expressed M protein by any method for detecting the protein such as for example, immunoblotting an extract using an antibody specific for the M protein. FIG. 1 illustrates western blotting to determine the absence of expressed M protein in one M negative mutant (M18Ω, described hereafter) using antisera prepared against a each of; a native M protein (rM18) from a Type 18 *Streptococcus*; a 30 amino acid N-terminal peptide of the M18 protein, (SM18(1–30); and an internal fragment from a Type 5 *Streptococcus* M protein (SM5(265–291). (see also Example 1).

One purpose of making an M-negative *Streptococcus* mutant is to facilitate detection of non-M protein surface antigens which contain opsonic epitopes. An M-negative mutant suitable for identifying a Spa antigen preferably exhibits continued virulence in a mammalian system because non-virulent strains are less likely to elicit opsonic antibodies. Virulence of an M-negative mutant may be tested by several methods known in the art. One method is grow the strain in mammalian blood and to score virulence by the number of generations of growth obtained in the blood culture. Typically, a virulent strain will grow for at least 4 generations after three hours of culture in mammalian blood. Typically, a test for virulence in blood uses blood obtained from an animal for which protection against Streptococcal infection is sought. In one practice of this invention, an M18 parent strain used to produce the M-negative mutant M18Ω grew for 8 generations after a three hour rotation in human blood. The M18Ω mutant showed similar virulence by growing for 7.5 generations under the same conditions. (See Example 1).

Another method for assessing virulence is by an intraperitoneal challenge infection. Briefly, this method determines the does of bacterial particles necessary to be lethal in a test animal, usually a mouse. Virulence is scored by calculating the number of bacteria that is lethal to 50% of test animals after intraperitoneal injection (LD50). Typically, a virulent strain will have an LD50 of less than $10^6$ in a mouse. For example, the M18 parent strain discussed above had an LD50 of $0.73\times10^5$ while the M18Ω mutant had an LD50 of $1.26\times10^5$. Optionally, the lethality of the mutant bacteria can be confirmed by recovering live bacteria from the spleens of test animals which succumb to the injection and testing for the presence of identifying characteristics of the mutant, such as for example, drug resistance or maintenance of the M-negative phenotype.

Once a virulent M-negative *Streptococcus* mutant has been obtained, the presence of a Spa polypeptide can be initially assessed by scoring for the presence of opsonizing epitopes on the surface of the mutant bacteria. The ordinarily skilled artisan will recognize a variety of in vivo and in vitro methods of testing for the presence of opsonizing epitopes. One method is to raise antisera against a crude surface peptide fraction (pep) released from the surface of bacterial particles after treating bacterial particles with a protease, and then to use the antisera in an in-vitro opsonization assay.

Many proteases are known in the art are suitable for the preparation of a crude surface peptide fraction from the surface of bacteria. Usually a protease which cleaves many different peptide linkages, such as for example pepsin, is incubated with a bacterial particles under reaction conditions that are suboptimal for the activity of the protease and/or with an amount of protease selected to yield a mixture enriched with larger rather than smaller polypeptides. Guidance for reaction conditions useful for releasing surface peptides from Streptococci particles may be found in part by the disclosure provided herein. (See Examples 3 and 4). Antisera against the crude surface peptide fraction may be raised in several species, typically mammals and, most typically rabbits. Methods of raising antisera against a peptide fraction are well known in the art and some of these are described hereafter.

An example in vitro opsonization assay useful in the practice of this invention is an opsonophagocytosis assay which detects phagocytosis facilitated by the presence of opsonizing antibodies present in a test antisera. Briefly, the assay measures the amount of phagocytosis of selected bacterial particles after preincubating the particles in the presence or absence of antisera raised against a sample of antigens obtained from the test bacteria. Preincubation with the antisera coats the particles with reactive antibodies, some of which will be opsonic antibodies elicited from opsonic epitopes present on the surface of the bacterial particles. Preincubated coated particles are then mixed with whole blood from an animal, typically a mammal for which opsonic protection is to be sought (e.g., a human) to determine the percentage of neutrophils that associate with the bacterial particles which is a measure of phagocytic activity facilitated by opsonic antibodies. Antisera containing opsonic antibodies induce a higher percentage of neutrophils associated with the selected bacteria than does antisera lacking opsonic antibodies. In a variation of this test, the bactericidal activity of antisera can be tested by incubating the antisera with fewer bacterial particles, incubating in blood for a longer period of time and then plating the mixture on a culture medium to score for viable bacteria. The presence of opsonic antibodies in the antisera increase the number of bacteria destroyed by phagocytosis and therefore lowers the number of colony forming units (CFUs) detected on the plate culture.

One advantage of these assays is that bacteria particles can be selected to score for serotype and strain specificity of opsonic epitopes. Thus, antisera raised against crude surface peptides obtained from one serotype may be tested for the ability to provide opsonic protection against other serotypes by scoring for opsonophagocytosis or bactericidal activity against the other serotypes. In addition, the presence of a novel opsonic polypeptide, such as the Spa antigen of the present invention, can be detected by comparing the ability of different antisera raised against different surface antigen preparations to provide opsonic protection against different strains. For example, in one embodiment of this invention, antisera raised against crude surface peptides obtained from the M18 parent strain provided opsonic protection against both the parent and the M18Ω mutant, however, antisera raised against purified M protein of the parent (M18 protein) or an N-terminal fragment thereof only provided protection against the parent and not the mutant strain. (See Example 3) This indicates for the first time, that a *Streptococcus* species contains opsonic epitopes on its surface that differ from the previously known opsonic epitopes of the M protein class.

In a similar fashion, antisera raised against crude surface peptides from the M18Ω mutant were shown to provide opsonic protection against not only itself, but against the M18 parent and other Streptococcal serotypes as well. In one example, opsonic protection was provided against at three-serotypes of group A Streptococci including Type 3, Type 18 and Type 28. This indicates the mutant displays a novel opsonic epitope other than M protein which is capable of providing opsonic protection across multiple Streptococci serotypes. Thus, although the parent, the mutant and other serotypes display the novel opsonic epitope (Spa) this epitope is readily shown to be distinct from M protein by showing the M negative mutant expressed the epitope even while M protein is not expressed. Identification of a virulent, M-negative *Streptococcus* mutant provides a first step in a general method for the identification and isolation of the Spa polypeptides and antigens of the present invention.

Identification of the polypeptide containing a Spa antigen is accomplished by separating the surface polypeptides of a *Streptococcus* and identifying a fraction that possesses the opsonic epitope indicative of the Spa antigen. In one method, the surface polypeptide to be separated is comprised of the crude surface peptide mixture obtained by protease treatment of an M-negative *Streptococcus* mutant shown to display an opsonic epitope other than M protein. Preferably, separation is performed to isolate the Spa polypeptide from other peptides present in the crude surface peptide mixture. One skilled in the art is able to envision numerous protocols for separating a crude surface peptide mixture including but not limited to a wide spectrum of electrophoresis and chromatography techniques particularly designed for separating polypeptides.

Figure 2:
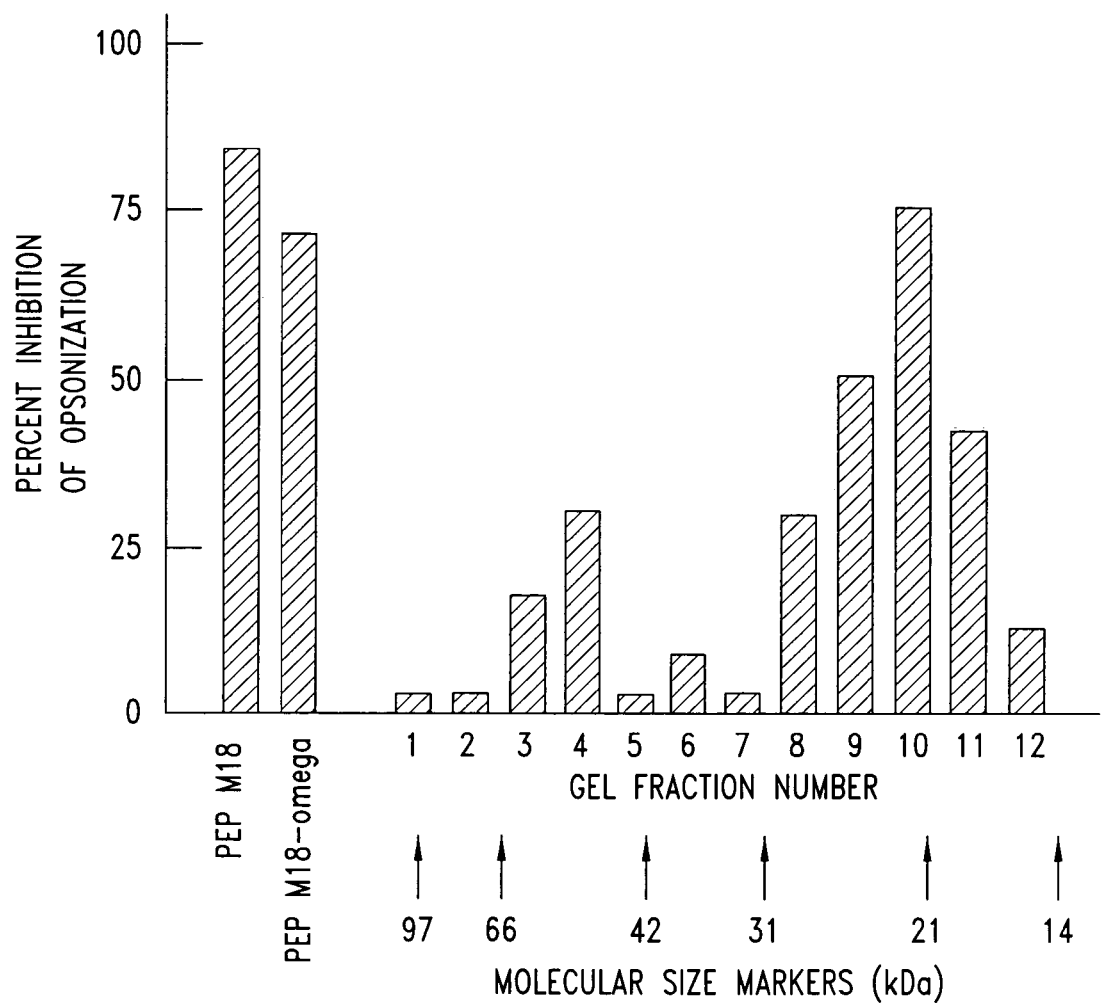
FIG. 2 illustrates identification of Spa in a crude pepsin extract of M18Ω. The extract was separated by preparative polyacrylamide gel electrophoresis and the entire gel was transferred to nitrocellulose paper. The ends of the paper were cut vertically and stained with Coomassie® blue. The center section was cut into horizontal strips approximately 10–12 mm in width and each one is identified as a fraction number. These strips were cut into smaller pieces and used as to absorb opsonic antibodies from a rabbit antiserum against crude pep M18Ω. Opsonization assays were performed using the M18Ω strain, each absorbed antiserum, and antisera inhibited with 1 mg/ml of pep M18 or pep M18Ω. Percent inhibition was based on the level of opsonization achieved with the unabsorbed antiserum.

In a typical practice of this invention, a combination of polyacrylamide gel electrophoresis, antibody binding and opsonization inhibition assays are used to separate and identify Spa polypeptides containing opsonic epitopes. An example of use of this protocol is illustrated in FIG. 2. Briefly, a crude surface peptide mixture is separated on a preparative 10% SDS polyacrylamide gel and then immunoblotted onto nitrocellulose paper or other suitable blotting substrate. The nitrocellulose paper is cut into strips containing different fractions of the separated polypeptides and incubated with antisera prepared against the crude surface peptide mixture to absorb antibodies that bind to the separated polypeptides. The absorbed antisera are then used in an opsonization assay and compared to the results obtained with unabsorbed antisera. Opsonic polypeptides present on the nitrocellulose strips will absorb opsonic antibodies from the test antisera so that the residual antisera will show reduced activity (inhibition) in an opsonization assay in comparison to unabsorbed antisera. In a typical practice, a duplicate immunoblot is subjected to ordinary western blotting to confirm the presence of immunoreactive polypeptides. Additionally, a duplicate polyacrylamide gel can be prepared to aid in purification of polypeptides shown to contain opsonic epitopes by the opsonizations inhibition assays.

In one practice of the invention, the identified Spa polypeptide is isolated and purified by any polypeptide purification techniques known in the art. As used herein, to "isolate" means to take any step to separate a species from a milieu in which it naturally occurs, and to "purify" means to isolate a fraction wherein the desired species represents 50%–100% of all extracted polypeptides present in the fraction. For further characterization of Spa, it is preferred that the Spa polypeptide comprise at least 90% and more preferably at least 95% of polypeptides in the purified fraction. Typical isolation steps useful in the practice of this invention include, but are not limited to, ammonium sulfate precipitation, polyacrylamide gel electrophoresis and HPLC. These techniques are suitable to provide a Spa polypeptide of sufficient quantity and purity to obtain an N-terminal sequence and to raise specific antibodies in a mammal such as a rabbit.

Figure 3:
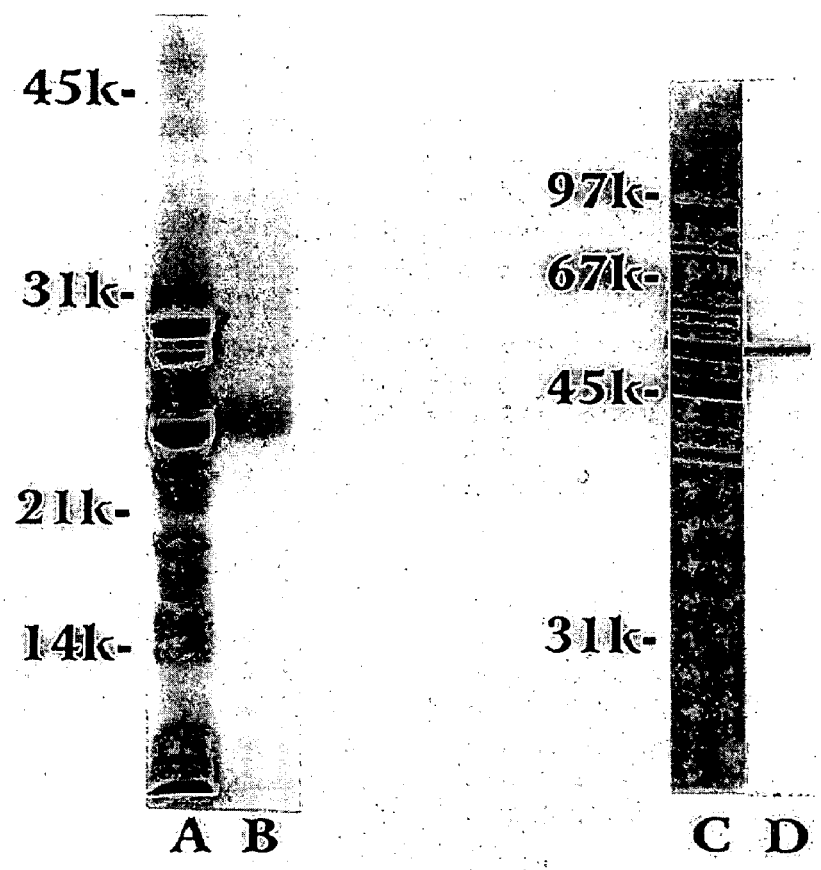
FIG. 3 shows polyacrylamide gel electrophoresis of a purified fragment of Spa (lanes A and B) and Western blot analysis of the native protein extracted by phage lysin (lanes C and D). The crude pep M18Ω (lane A) and the purified Spa (lane B) were electrophoresed in a 10% polyacrylamide gel under reducing conditions and stained with Coomassie® blue. The purified Spa migrated with an apparent molecular weight of 24 kDa. Western blot analysis was performed to identify the native Spa that was released from the cell wall of M18Ω by group C Streptococcal phage-associated lysin. The crude lysin extract contained multiple proteins that stained with Coomassie® blue (lane C). Antiserum against the synthetic peptide of Spa reacted with a single protein in the extract with an apparent M.W. of 50 kDa (lane D).

In one embodiment, a Spa polypeptide present in an group A, Type 18 *Streptococcus* was identified and purified using the aforementioned protocols with antisera obtained from the M18Ω mutant described above. The polypeptide was purified from a crude surface peptide fraction obtained from the mutant by using precipitation in 60% saturated ammonium sulfate, followed by dialysis, lyophilization, and preparative polyacrylamide gel electrophoresis. FIG. 3(A,B) shows that the isolated polypeptide is estimated to have a size of 24 kD as determined by analytical polyacrylamide gel electrophoresis. FIG. 3(C,D) shows a western blot analysis of native proteins released from the cell wall of M18Ω by phage associated lysin C and illustrates that the 24 kD Spa polypeptide is part of a larger native protein having an estimated size of 50 kD.

In another embodiment, a Spa polypeptide isolated according to the present invention is used to identify and isolate peptide antigens containing opsonic epitopes comprised of contiguous amino acids present on the N-terminus of a Spa polypeptide. One example is provided by SEQ. ID NO: 3. As used herein, "contiguous amino acids" is a sequence of amino acids which are identical to, or conservative variants of, a precise sequence of amino acids present on a Spa polypeptide. The Spa polypeptides of the present invention are isolated from a cell that expresses the polypeptide and which has a portion of the amino acid sequence of the polypeptide exposed on the outside surface of the cell. "Exposed on the outer surface" means the polypeptide has a portion extended through the outer membrane of the cell which is accessible to a proteases and/or to interaction with the major histocompatibility complex of an animal without having to rupture the cell. As used herein, the "N-terminus" is a sequence of about 240 amino acids or less that is present at or near the N terminal of a polypeptide that can be obtained after proteolytic cleavage of polypeptides exposed on the surface of a cell. Therefore, the term includes an N-terminus of a proteolytic fragment as well as an N-terminus of a native protein when the N-terminus of the native protein is exposed on the outer surface of a cell.

The N terminus of the Spa polypeptides of the present invention undoubtedly contains shorter peptide sequences that form opsonic epitopes because it is highly unlikely that opsonic antibodies recognize an epitope requiring the entire sequence of a polypeptide exposed to the outer surface of a cell. It is well known in the art that an epitope may consist of peptide sequence as small as 8 amino acids which is generally considered by those skilled in the art to be the lower size limit for a peptide to be capable of forming an epitope that can interact with the major histocompatibility complex (MHC). Therefore, another aspect of this invention includes polypeptides and peptides containing opsonic epitopes comprised of at least 8 contiguous amino acids from the N-terminus of an isolated Spa polypeptide. Identification of an opsonic amino acid sequence on the Spa polypeptides of the present invention may be accomplished by a variety of methods.

One method is to use chemical degradation of Spa to obtain peptide fragments and to test those peptide fragments or to synthetic peptides containing contiguous amino acids derived therefrom, for the presence of opsonic epitopes. In one practice of this invention, Edman degradation of the purified Spa polypeptide is used to provide a precise amino acid sequence for the N-terminus of the isolated polypeptide. In another embodiment, Edman degradation is used to provide a precise amino acid sequence of an internal fragment prepared by enzymatic or chemical digestion of the isolated polypeptide. For example, Edman degradation of the Spa polypeptide isolated from the M18Ω mutant described above provided two amino acid sequences: a first sequence of 23 amino acids comprising a portion of the N-terminus of the isolated polypeptide and a second sequence of 10 amino acids comprising a portion of an N-terminus of an internal peptide fragment that was isolated after LysC digestion of the polypeptide. The sequence of the 23 amino acid N-terminus is provided in SEQ. ID NO: 3 and shown in Example 4 along with the sequence of the internal fragment. While not wishing to be bound by speculation, it is believed that SEQ. ID NO: 3 represents the N-terminus of the native Spa protein, however, the possibility that the native Spa protein contains additional amino acids at the N-terminus cannot be excluded. A comparison to SEQ ID NO:5 shows that the native protein is processed from a preprotein by removal of a residue signal sequence.

When smaller peptide fragments or sequences are isolated from a Spa polypeptide, the isolated peptide fragments or sequences can be identified as containing an opsonic epitope by modification of the methods described above for identifying an opsonic polypeptide. The only modification required is use of a separation system suitable for the separation of smaller peptides. High percentage polyacrylamide gels and HPLC techniques are particularly suited for separating smaller peptides and such techniques are readily accessible to those skilled in the art. Alternatively, synthetic peptides can by made which are contiguous with the amino acid sequences deduced by Edman degradation. Therefore, embodiments of the present invention include peptides containing opsonic epitopes comprised of at least 8 contiguous amino acids of a Spa polypeptide.

In one embodiment, a peptide containing 23 contiguous amino acids of SEQ. ID NO: 3 which represents the N terminus of an isolated Spa polypeptide is chemically synthesized. That peptide, herein designated spa18(1–23) is shown to be opsonic by first chemically coupling it to a suitable carrier such as KLH and using it to raise antisera in rabbits. Another antiserum is made against the intact Spa polypeptide for comparison. These antisera are then used to show cross reactivity with antisera prepared from crude surface peptides obtained from an M-negative mutant such as M18Ω and to further show the presence of opsonic epitopes using the opsonization assays described above. Results demonstrate that the 23 amino acid peptide of the N terminus of the Spa polypeptide contains an opsonic epitope having a similar opsonizing capacity as that obtained from the whole isolated polypeptide and from the crude surface peptide fraction. Western blotting also shows that antisera to the purified protein and the 23 amino acid peptide does not bind to an M protein such as M18. Results further show that the 23 amino acid peptide and isolated Spa polypeptide produce antisera capable of providing opsonic protection against the parent M18 strain, the mutant strain and other serotypes of *Streptococcus*, while antisera prepared against M protein from the parent strain is only able to provide opsonic protection against the parent strain. (See Examples 5 and 6.)

While determining a precise amino acid sequence for an isolated Spa polypeptide or peptide epitopes contained therein is a preferred practice of this invention, it is not necessary to structurally define the isolated polypeptide at the sequence level to obtain the Spa polypeptides provided herein. The aforementioned description provides a method useful for isolating Spa polypeptides from any *Streptococcus* source, particularly from group A Streptococci. As is evident from the foregoing description, a Spa polypeptide is a polypeptide product having particular functional characteristics that fulfill requirements of the method and which are thereby isolated by practice of the method. To summarize, a Spa polypeptide is a polypeptide product obtained from a *Streptococcus* species which is displayed on the outer surface of a *Streptococcus* bacterium, and which contains antigenic epitopes other than the epitopes contained on an M protein. These epitopes represent opsonic antigens that do not cross react with antisera prepared against M-protein and which are capable of providing opsonic protection against multiple serotypes of Streptococci. These characteristics are found in a polypeptide isolated according to the practices described in this invention.

More particularly, this invention provides a method for identifying and isolating a non M protein Spa polypeptide of a *Streptococcus* species that elicits opsonic antibodies protective against multiple serotypes of Streptococci. The method includes the steps 1) producing a virulent mutant of the *Streptococcus* species that does not express an M protein; 2) obtaining antisera against a crude surface polypeptide fraction obtained from the mutant; 3) determining that the antisera contains opsonic antibodies that do not cross react with M protein and which provide opsonic protection against the mutant; 4) separating polypeptides in the extract to obtain isolated polypeptide fractions; 5) screening the isolated polypeptide fractions with antisera containing opsonic antibodies to identify Spa polypeptides that contain opsonic epitopes; 6) purifying the polypeptide identified as having opsonic epitopes; and 7) testing the purified polypeptides to determine that they elicit opsonic antibodies that are protective against multiple serotypes of Streptococci.

Therefore, another embodiment of this invention includes Spa polypeptides isolated according to this method. The skilled artisan will immediately recognize that this method enables the isolation of a variety of Spa polypeptides from a variety of Streptococcus species. Thus, for example, while the Spa polypeptide isolated from an M18 mutant exemplified in one practice of this invention is protective against at least three serotypes of Streptococci (See Example 6) other Spa polypeptides isolated from other Streptococci can be isolated that are protective against other serotypes of Streptococci.

II. Nucleic Acids

Another aspect of the present invention is isolated nucleic acid molecules comprising a sequence that encodes a Streptococcus Spa polypeptide. This aspect of the invention pertains to isolated nucleic sequences encoding a Spa polypeptide (i.e. a spa gene) as well as those sequences readily derived from isolated nucleic molecules such as for example complementary sequences, reverse sequences and complements of reverse of sequences.

In one embodiment, the isolated nucleic acid molecule is comprised of a sequence selected from SEQ. ID NOS: 1 or 4, a complement of SEQ. ID NOS: 1 or 4 or variants thereof. Variants of the nucleic acid sequences include variants selected from sequences that encode the polypeptide of SEQ. ID NOS: 2 or 5 which are degenerate to SEQ. ID NOS: 1 or 5 because of the genetic code; sequences that encode a polypeptide which has conservative amino acid substitutions to the polypeptide of SEQ. ID NOS: 2 or 5, or sequence that encode a polypeptide that is at least 50% identical to SEQ. ID NO: 2 or 5. In still another embodiment, the invention provides an isolated nucleic acid molecule comprising a sequence that hybridizes to the aforementioned nucleic acid molecules under conditions of high stringency. Another embodiment includes isolated nucleic acid molecules comprising a sequence that encodes an opsonic epitope form a Spa polypeptide. A related aspect of the nucleic acid sequences provided herein include nucleic acid molecules encoding an opsonic epitope and further encoding a fusion polypeptide wherein the fusion polypeptide contains the opsonic epitope fused to at least one other polypeptide sequence. In one embodiment, the other peptide sequence includes a tag sequence that facilitates isolation of the fusion polypeptide from a cellular extract. In another embodiment the other peptide sequence is a carrier protein.

A related embodiment to the aforementioned nucleic acid molecules includes a vector comprising those nucleic acid molecules operably linked to a promoter so that the vector expresses a polypeptide encoded by the isolated nucleic acid when the vector is introduced into a host cell. In another embodiment, the invention provides a host cell carrying such a vector.

As used herein, a spa gene is a Streptococcus gene or nucleic acid variant thereof, that encodes at least 100 amino acids of a Spa polypeptide including for example, the isolated nucleic acid of SEQ. ID NOS: 1 or 4, a nucleic acid that encodes a 24 kDa Spa polypeptide or a nucleic acid that encodes a native Spa protein of about 50 kDa. One example of part of a spa gene is set forth in FIG. 4, and in SEQ ID NOS:1–2 which provides a nucleotide and amino acid sequence from one spa gene isolated from a Type 18 Streptococcus. Another example is set forth in FIGS. 5 and 6 that shows full-length nucleic acid and amino acid sequences according to SEQ ID NOS: 4 and 5, respectively. These represent full-length spa sequences and that include a signal peptide of 37 residues that is cleaved to produce a mature spa protein, as indicated.

Another aspect of the isolated spa nucleic acids of this invention includes fragments of isolated sequences. As used herein, a "fragment" of an isolated spa gene includes any nucleic acid sequence comprising at least 12 nucleotides from an isolated spa gene or a variant of at least 12 nucleotides that hybridizes to an isolated spa gene under conditions of moderate or high stringency. Such sequences are useful for a variety of purposes including PCR primers for isolating additional spa sequences or variants thereof from other Streptococci. Another typical use is for recombinant expression of a peptide or polypeptide comprised of epitopes present on a native Spa polypeptide.

Also provided herein are nucleic acid fragments or oligonucleotides useful as probes and primers for identifying or obtaining Spa sequences. More specifically, a nucleic acid fragment or oligonucleotide that comprise at least 12 contiguous nucleotides of SEQ ID NO:1 or 4 are particularly useful for hybridization to Spa nucleic acid sequences and/or for primers that can be used to amplify the same. More particular embodiments include nucleic acid fragments or oligonucleotides where the length is at least 18, 24, 30, 50 or greater than 50 nucleotides. Complements of the above sequences are also included.

Another embodiment of nucleic acid fragments or oligonucleotides of this invention include those that encode a peptide epitope that can be detected, for example, by the ability to specifically bind to a Spa antibody or which can be used to elicit an immune response in an animal. Useful peptide epitopes are those capable of eliciting antibodies that specifically bind to the peptide or polypeptide comprised of the Spa amino acid residues, or that are capable of eliciting a T-cell response to the same. Peptide sequences of 8 or more amino acids are useful in this regard since it is generally understood by those skilled in the art that 8 amino acids is the lower size limit for a peptide to interact with the major histocompatibility complex (MHC). More preferred embodiments include nucleic acid fragments or oligonucleotides encoding at least 10, 15 or 20 amino acids.

Accordingly, the present invention provides nucleic acid fragments or oligonucleotides encoding a peptide comprised of at least 8 contiguous amino acids of the sequence according to SEQ ID NO:2, 3 or 5. Particular embodiments of this aspect include nucleic acid fragments or oligonucleotides encoding a peptide comprised of at least 10, 15, or 20 amino acids. Preferred embodiments include nucleic acid fragments wherein the encoded peptide comprises sequences from the N-terminus of a Spa polypeptide, and more particularly, sequences that encode opsonic epitopes. These include for example, sequences encoding peptides contained within SEQ ID NO: 2 or 3, or from an N-terminus of an internally located peptide isolated after cleavage of a larger Spa polypeptide such as for example, SEQ ID NO:5.

The invention also provides nucleic acids useful for modulating or inhibiting the expression of a Spa polypeptide in a cell. More specifically, the invention provides for ribozymes that cleaves RNA encoding the aforementioned Spa polypeptides and for antisense molecules that bind to such an RNA. This includes nucleic acid molecules comprising a sequence that encodes such a ribozyme or antisense molecule and vectors comprising the same. Particular embodiments include vectors wherein the aforementioned ribozyme or antisense nucleic acid is operably linked to a promoter. Typical embodiments of these vectors are selected from the group consisting of plasmid vectors, phage vectors, herpes simplex viral vectors, adenoviral vectors, adenovirus-associated viral vectors and retroviral vectors. Host cells comprising the above vectors are also included.

Ribozymes are provided which are capable of inhibiting expression of Spa RNA. As used herein, "ribozymes" are intended to include RNA molecules that contain anti-sense sequences for specific recognition, and an RNA-cleaving enzymatic activity. The catalytic strand cleaves a specific site in a target RNA at greater than stoichiometric concentration. A wide variety of ribozymes may be utilized within the context of the present invention, including for example, the hammerhead ribozyme (for example, as described by Forster and Symons, *Cell* 48:211–220, 1987; Haseloff and Gerlach, *Nature* 328:596–600, 1988; Walbot and Bruening, *Nature* 334:196, 1988; Haseloff and Gerlach, *Nature* 334: 585, 1988); the hairpin ribozyme (for example, as described by Haseloffet al., U.S. Pat. No. 5,254,678, issued Oct. 19, 1993 and Hempel et al., European Patent Publication No. 0 360 257, published Mar. 26, 1990); and *Tetrahymena* ribosomal RNA-based ribozymes (see Cech et al., U.S. Pat. No. 4,987,071). Ribozymes of the present invention typically consist of RNA, but may also be composed of DNA, nucleic acid analogs (e.g., phosphorothioates), or chimerics thereof (e.g., DNA/RNA/RNA).

Antisense oligonucleotide molecules are provided which specifically inhibit expression of Spa nucleic acid sequences (see generally, Hirashima et al. in *Molecular Biology of RNA:New Perspectives* (M. Inouye and B. S. Dudock, eds., 1987 Academic Press, San Diego, p. 401); *Oligonucleotides: Antisense Inhibitors of Gene Expression* (J. S. Cohen, ed., 1989 MacMillan Press, London); Stein and Cheng, *Science* 261:1004–1012, 1993; WO 95/10607; U.S. Pat. No. 5,359, 051; WO 92/06693; and EP-A2-612844). Briefly, such molecules are constructed such that they are complementary to, and able to form Watson-Crick base pairs with, a region of transcribed Spa mRNA sequence. The resultant double-stranded nucleic acid interferes with subsequent processing of the mRNA, thereby preventing protein synthesis (Example 6).

Within a related aspect, any of the aforementioned nucleic acids may include modified nucleotides. Modified nucleotides can have modifications in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as azasugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid" also includes so-called "peptide nucleic acids," which comprise naturally-occurring or modified nucleic acid bases attached to a polyamide backbone. Nucleic acids can be either single stranded or double stranded.

It should be understood that spa genes include nucleic acid sequences encoding wild-type/native Spa polypeptides, as well as other variants (including alleles). Briefly, such variants may result from natural polymorphisms or be synthesized by recombinant methodology or chemical synthesis, and differ from wild-type polypeptides by one or more amino acid substitutions, insertions, deletions, or the like. Variants encompassing conservative amino acid substitutions include, for example, substitutions of one aliphatic amino acid for another, such as Ile, Val, Leu, or Ala or substitutions of one polar residue for another, such as between Lys and Arg, Glu and Asp, or Gln and Asn. Such substitutions are well known in the art to provide variants having similar physical properties and functional activities such as for example, the ability to elicit and cross react with similar antibodies. Other variants include nucleic acids sequences that encode a polypeptide having at least 50%, 60%, 70%, 80%, 90% or 95% amino acid identity to SEQ ID NO:2, 3 or 5. Preferred embodiments are those having greater than 90% or 95% identity with the amino acid sequence of SEQ. ID NOS: 2 or 3 or 5. As will be appreciated by those of ordinary skill in the art, a nucleotide sequence encoding an Spa or a variant may differ from the native sequences presented herein due to codon degeneracy, nucleotide polymorphisms, or nucleotide substitutions, deletions or insertions.

While particular embodiments of such isolated nucleic acids are depicted in SEQ ID NOS:1 and 4 and FIGS. 4 and 5, within the context of the present invention, reference to one or more isolated nucleic acids includes variants of these sequences that are substantially similar in that they encode native or non native proteins, polypeptides or peptides with similar structure and function to the Spa polypeptide of SEQ. ID NOS: 2 or 5. As used herein, the nucleotide sequence is deemed to be "substantially similar" if: (a) the nucleotide sequence is derived from the coding region of a spa gene isolated from a *Streptococcus* (including, for example, portions of the sequence or allelic variations of the sequences discussed above) and contains a non-M protein epitope with substantially the same ability to elicit opsonic antibodies protective against Streptococci. or (b) the nucleotide sequence is capable of hybridization to the nucleotide sequences of the present invention under high stringency (e.g., capable of selectively hybridizing to nucleotide sequences a spa gene at least 42° C. overnight in the presence of salts and/or formamide at least as stringent as 6×SSC and 50% formamide); or (c) the nucleotide sequences are degenerate (i.e., sequences which code for the same amino acids using a different codon sequences) as a result of the genetic code to the nucleotide sequences defined in (a) or (b); or (d) is a complement of any of the sequences described in (a), (b) or (c).

Another aspect of the present invention is the use of isolated spa nucleotide sequences to produce recombinant proteins for immunizing an animal. Therefore, the use of any length of nucleic acid disclosed by the present invention (preferably 24 nucleotides or longer) which encodes a polypeptide or fragment thereof of at least 8 contiguous amino acids which is capable of binding to the major histocompatibility complex and eliciting or enhancing an immunogenic response is contemplated by this invention. Preferred embodiments include polypeptides or fragments thereof that elicit opsonic antibodies. Immunogenic response can be readily tested by known methods such as challenging a mouse or rabbit with polypeptides or fragments of interest and thereafter collecting antisera and determining if the antibody of interest is present. Other assays particularly useful for the detection of T-cell responses include proliferation assays, T-cell cytotoxicity assays, assays for delayed hypersensitivity and assays for opsonization such as previously described. In determining whether an antibody specific for an antigen of interest is produced by the animal, many diagnostic tools are available, including for example, testing binding of antigen to antibodies contained in a sample antisera using conventional western blotting, or using enzyme-linked immunoassays with a tag attached to the antigen of interest.

The isolated nucleic acids encoding Spa polypeptides according to this invention can be obtained using a variety of methods. For example, a nucleic acid molecule can be obtained from a cDNA or genomic expression library by screening with an antibody or antibodies reactive with a Spa polypeptide (see, e.g., Sambrook et al., *Molecular Cloning: A Laboratory Manual*, Cold Spring Harbor, 1989; Ausubel et al., *Current Protocols in Molecular Biology*, Greene Publishing, 1987). Further, random-primed PCR can be employed (see, e.g., *Methods in Enzymol.* 254:275, 1995). In addition, variations of random-primed PCR can also be used, especially when a particular gene or gene family is desired. In one such method, one of the primers is a random primer and the other is a degenerate primer based on the amino acid sequence or nucleotide sequence encoding a Spa polypeptide. This method is exemplified for example, in Example 7 where a codon degenerate primer designed to bind to a sequence that encodes any one of several variants of a 23 amino acid N terminus of an isolated Spa polypeptide was used to isolate a 346 nucleotide sequence of a spa gene which is depicted in FIG. 4 and SEQ. ID NO: 1.

Other methods can also be used to obtain isolated nucleic acid molecules that encode a Spa polypeptide. For example, a nucleic acid molecule can be isolated by using the sequence information provided herein to synthesize a probe which can be labeled, such as with a radioactive label, enzymatic label, protein label, fluorescent label, or the like, and hybridized to a genomic library or a cDNA library constructed in a phage, plasmid, phagemid, or viral vectors designed for replication or expression in selected host cells (see, e.g., Sambrook et al. (supra); Ausubel et al. (supra)). DNA representing RNA or genomic nucleic acid sequence can also be obtained by amplification using sets of primers complementary to 5' and 3' sequences of the isolated nucleic acid sequences provided in SEQ. ID NO: 1 or to variants thereof as described above. For ease of cloning, restriction sites can also be incorporated into the primers.

Variants (including alleles) of the isolated spa nucleic acid sequence provided herein can be readily obtained from natural variants (e.g., polymorphisms, mutants and other serotypes) either synthesized or constructed. Many methods have been developed for generating mutants (see generally Sambrook et al. (supra); Ausubel et al. (supra)). Briefly, preferred methods for generating nucleotide substitutions utilize an oligonucleotide that spans the base or bases to be mutated and contains the mutated base or bases. The oligonucleotide is hybridized to complementary single stranded nucleic acid and second strand synthesis is primed from the oligonucleotide. The double-stranded nucleic acid is prepared for transformation into host cells, such as *E. coli*, other prokaryotes, yeast or other eukaryotes. Standard screening and vector growth protocols are used to identify mutant sequences and obtain high yields.

Similarly, deletions and/or insertions of spa genes can be constructed by any of a variety of known methods. For example, the gene can be digested with restriction enzymes and/or nucleases and be religated such that sequences are deleted or religated with additional sequence such that an insertion or large substitution is made. Similarly, a variety of transposons and other insertional elements may be used to make recombinants having deletions and insertions Thus, in one example, a spa mutant containing a Ω insertional element in a spa gene can be made in a manner similar to the making of the M18Ω described above. Other means of generating variant sequences, known in the art, can be employed, for examples see Sambrook et al. (supra) and Ausubel et al. (supra). Moreover, verification of variant sequences is typically accomplished by restriction enzyme mapping, sequence analysis or hybridization. Variants which encode a polypeptide that elicits an immunogenic response specific to a Spa polypeptide are particularly useful in the context of this invention.

As noted above, the present invention provides isolated or purified Spa polypeptides proteins and peptides as those terms have been previously defined herein. In one aspect, these isolated or purified materials may be obtained from a host cell expressing a recombinant nucleic acid that encodes Spa polypeptides proteins or peptides which may be isolated from the host cell. The Spa polypeptides of the present invention can be purified by a variety of standard methods with or without a protease treatment or polyacrylamide electrophoresis step, and/or may be isolated from organisms other than Streptococci which have been engineered to express an isolated spa nucleic acid. For example, a Spa polypeptide of the present invention can be isolated by, among other methods, culturing suitable host and vector systems to produce a native Spa protein, polypeptide, fusion protein or peptide fusion using recombinant DNA methods (discussed further herein). Using these methods Spa may be engineered to be exported from the host cell, retained within the host cell, for example within inclusion bodies, or integrated into the surface of host cell as is the case for natural Spa expression in Streptococci. When engineered for export, a supernatant from a culture of the host cell can be used to isolate exported Spa polypeptides. When integrated into the surface, Spa polypeptides may be obtained by protease treatment to obtain a crude surface peptide fraction as previously described. When expressed in inclusion bodies, Spa proteins, fusion peptides and the like, can be obtained by a variety of purification procedures. For example, a Spa-containing extract can be applied to a suitable purification matrix such as a Spa antibody bound to a suitable support. Alternatively, anion or cation exchange resins, gel filtration or affinity, hydrophobic or reverse phase chromatography may be employed in order to purify the protein. The Spa polypeptide can also be concentrated using commercially available protein concentration filters, such as an Amicon or Millipore Pellicon ultrafiltration unit, or by vacuum dialysis.

In one example of isolating Spa polypeptides, proteins or peptides by recombinant methods, an isolated nucleic acid encoding a Spa protein, polypeptide, or peptide can be expressed as a histidine-tagged molecule, permitting purification on a nickel-chelating matrix. Alternatively, other tags may be used, including FLAG and GST. The associated tag can then be removed in the last step of purification, for example, for certain vectors, His-tagged proteins may be incubated with thrombin, resulting in cleavage of a recognition sequence between the tag and the Spa polypeptide (e.g., pET vectors from Invitrogen).

It is well known in the art that certain vectors (e.g., pUC) can be used for producing multiple copies of a nucleotide molecule of interest as well as being useful for genetic manipulation techniques (e.g., site-directed mutagenesis). See Sambrook (supra). Of particular interest to this disclosure are expression vectors. The expression vector includes transcriptional promoter/enhancer elements operably linked to an isolated nucleic acid molecule encoding a Spa polypeptide. The expression vector may be composed of either deoxyribonucleic acids ("DNA"), ribonucleic acids ("RNA"), or a combination of the two (e.g., a DNA-RNA chimera). Optionally, the expression vector may include a polyadenylation sequence or one or more restriction sites. Additionally, depending on the host cell chosen and the expression vector employed, other genetic elements such as an origin of replication, additional nucleic acid restriction sites, enhancers, sequences conferring inducibility of transcription, and genes encoding proteins suitable for use as selectable or identifiable markers, may also be incorporated into the expression vectors described herein.

The manipulation and expression of spa genes can be accomplished by culturing host cells containing an expression vector capable of expressing the spa genes. Such vectors or vector constructs include either synthetic or cDNA-derived nucleic acid molecules or genomic DNA fragments encoding the Spa polypeptides, which are operably linked to suitable transcriptional or translational regulatory elements. Suitable regulatory elements within the expression vector can be derived from a variety of sources, including bacterial, fungal, viral, mammalian, insect, or plant genes. Selection of appropriate regulatory elements is dependent on the host cell chosen, and can be readily accomplished by one of ordinary skill in the art in light of the present specification. Examples of regulatory elements include a transcriptional promoter and enhancer or RNA polymerase binding sequence, a transcriptional terminator, and a ribosomal binding sequence, including a translation initiation signal.

Nucleic acid molecules that encode any of the Spa protein, polypeptides, or peptides described above can be expressed by a wide variety of prokaryotic and eukaryotic host cells, including bacterial, mammalian, yeast or other fungi, viral, insect, and plant cells. The selection of a host cell may also assist the production of post-transitionally modified Spa polypeptides, depending upon the desires of the user. Methods for transforming or transfecting such cells to express nucleic acids are well known in the art (see, e.g., Itakura et al., U.S. Pat. No. 4,704,362; Hinnen et al., *PNAS USA* 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al., *Molecular Cloning: A Laboratory Manual, 2nd* edition, Cold Spring Harbor Laboratory Press, 1989; for plant cells see Czako and Marton, *Plant Physiol.* 104: 1067–1071, 1994; Paszkowski et al., *Biotech.* 24:387–392, 1992).

Bacterial host cells suitable for carrying out the present invention include but are not limited to, numerous strains of *E. coli*, as well as various strains of *M leprae, M. tuberculosis, M. bovis, B. subtilis, Salmonella typhimurium*, and various species within the genera *Pseudomonas, Streptomyces, Streptococcus*, and *Staphylococcus*, as well as many other bacterial species well known to one of ordinary skill in the art.

Bacterial expression vectors preferably comprise a promoter, which functions in the host cell, one or more selectable phenotypic markers, and a bacterial origin of replication. Representative promoters include the β-lactamase (penicillinase) and lactose promoter system (see Chang et al., *Nature* 275:615, 1978), the T7 RNA polymerase promoter (Studier et al., *Meth. Enzymol.* 185:60–89, 1990), the lambda promoter (Elvin et al., *Gene* 87:123–126, 1990), the trp promoter (Nichols and Yanofsky, *Meth. in Enzymology* 101:155, 1983) and the tac promoter (Russell et al., *Gene* 20:231, 1982). Representative selectable markers include various antibiotic resistance markers such as the kanamycin or ampicillin resistance genes. Many plasmids suitable for transforming host cells are well known in the art, including among others, pBR322 (see Bolivar et al., *Gene* 2:95, 1977), the pUC plasmids pUC18, pUC19, pUC118, pUC119 (see Messing, *Meth. in Enzymology* 101:20–77, 1983; Vieira and Messing, *Gene* 19:259–268, 1982), and pNH8A, pNH16a, pNH18a, and Bluescript M13 (Stratagene, La Jolla, Calif.). In one particular embodiment of this invention exemplified in Example 7, a 346 bp isolated nucleic acid encoding a Spa polypeptide was ligated into a pCR2.1-TOPO vector and expressed in *E. coli*.

Fungal host cells suitable for carrying out the present invention include, among others, *Saccharomyces pombe, Saccharomyces cerevisiae*, the genera *Pichia* or *Kluyveromyces* and various species of the genus *Aspergillus* (McKnight et al., U.S. Pat. No. 4,935,349). Suitable expression vectors for yeast and fungi include, among others, YCp50 (ATCC No. 37419) for yeast, and the amdS cloning vector pV3 (Turnbull, *Bio/Technology* 7:169, 1989), YRp7 (Struhl et al., *Proc. Natl. Acad. Sci. USA* 76:1035–1039, 1978), YEp13 (Broach et al., *Gene* 8:121–133, 1979), pJDB249 and pJDB219 (Beggs, *Nature* 275:104–108, 1978) and derivatives thereof.

Preferred promoters for use in yeast include promoters from yeast glycolytic genes (Hitzeman et al., *J. Biol. Chem.* 255:12073–12080, 1980; Alber and Kawasaki, *J. Mol. Appl. Genet.* 1:419–434, 1982) or alcohol dehydrogenase genes (Young et al., in *Genetic Engineering of Microorganisms for Chemicals*, Hollaender et al. (eds.), p. 355, Plenum, N.Y., 1982; Ammerer, *Meth. Enzymol.* 101:192–201, 1983). Examples of useful promoters for fungi vectors include those derived from *Aspergillus nidulans* glycolytic genes, such as the adh3 promoter (McKnight et al., *EMBO J.* 4:2093–2099, 1985). The expression units may also include a transcriptional terminator. An example of a suitable terminator is the adh3 terminator (McKnight et al., ibid., 1985).

As with bacterial vectors, the yeast vectors will generally include a selectable marker, which may be one of any number of genes that exhibit a dominant phenotype for which a phenotypic assay exists to enable transformants to be selected. Preferred selectable markers include those that complement host cell auxotrophy, provide antibiotic resistance or enable a cell to utilize specific carbon sources, and include leu2 (Broach et al., ibid.), ura3 (Botstein et al., *Gene* 8:17, 1979), or his3 (Struhl et al., ibid.). Another suitable selectable marker is the cat gene, which confers chloramphenicol resistance on yeast cells.

Techniques for transforming fungi are well known in the literature, and have been described, for instance, by Beggs (ibid.), Hinnen et al.(*Proc. Natl. Acad. Sci. USA* 75:1929–1933, 1978), Yelton et al. (*Proc. Natl. Acad. Sci. USA* 81:1740–1747, 1984), and Russell (*Nature* 301:167–169, 1983). The genotype of the host cell may contain a genetic defect that is complemented by the selectable marker present on the expression vector. Choice of a particular host and selectable marker is well within the level of ordinary skill in the art in light of the present specification.

Protocols for the transformation of yeast are also well known to those of ordinary skill in the art. For example, transformation may be readily accomplished either by preparation of spheroplasts of yeast with DNA (see Hinnen et al., *PNAS USA* 75:1929, 1978) or by treatment with alkaline salts such as LiCl (see Itoh et al., *J. Bacteriology*

153:163, 1983). Transformation of fungi may also be carried out using polyethylene glycol as described by Cullen et al. (*Bio/Technology* 5:369, 1987).

Viral vectors include those that comprise a promoter that directs the expression of an isolated nucleic acid molecule that encodes a Spa polypeptide as described above. A wide variety of promoters may be utilized within the context of the present invention, including for example, promoters such as MoMLV LTR, RSV LTR, Friend MuLV LTR, adenoviral promoter (Ohno et al., *Science* 265: 781–784, 1994), neomycin phosphotransferase promoter/enhancer, late parvovirus promoter (Koering et al., *Hum. Gene Therap.* 5:457–463, 1994), Herpes TK promoter, SV40 promoter, metallothionein IIa gene enhancer/promoter, cytomegalovirus immediate early promoter, and the cytomegalovirus immediate late promoter. The promoter may also be a tissue-specific promoter (see e.g., WO 91/02805; EP 0,415, 731; and WO 90/07936). In addition to the above-noted promoters, other viral-specific promoters (e.g., retroviral promoters (including those noted above, as well as others such as HIV promoters), hepatitis, herpes (e.g., EBV), and bacterial, fungal or parasitic-specific (e.g., malarial-specific) promoters may be utilized in order to target a specific cell or tissue which is infected with a virus, bacteria, fungus or parasite.

Thus, Spa polypeptides of the present invention may be expressed from a variety of viral vectors, including for example, herpes viral vectors (e.g., U.S. Pat. No. 5,288,641), adenoviral vectors (e.g., WO 94/26914, WO 93/9191; Kolls et al., *PNAS* 91(1):215–219, 1994; Kass-Eisler et al., *PNAS* 90(24):11498–502, 1993; Guzman et al., *Circulation* 88(6): 2838–48, 1993; Guzman et al., *Cir. Res.* 73(6):1202–1207, 1993; Zabner et al., *Cell* 75(2):207–216, 1993; Li et al., *Hum Gene Ther.* 4(4):403–409, 1993; Caillaud et al., *Eur. J. Neurosci.* 5(10):1287–1291, 1993; Vincent et al., *Nat. Genet.* 5(2):130–134, 1993; Jaffe et al., *Nat. Genet.* 1(5): 372–378, 1992; and Levrero et al., *Gene* 101(2):195–202, 1991), adenovirus-associated viral vectors (Flotte et al., *PNAS* 90(22):10613–10617, 1993), baculovirus vectors, parvovirus vectors (Koering et al., *Hum. Gene Therap.* 5:457-463, 1994), pox virus vectors (Panicali and Paoletti, *PNAS* 79:4927–4931, 1982; and Ozaki et al., *Biochem. Biophys. Res. Comm.* 193(2):653–660, 1993), and retroviruses (e.g., EP 0,415,731; WO 90/07936; WO 91/0285, WO 94/03622; WO 93/25698; WO 93/25234; U.S. Pat. No. 5,219,740; WO 93/11230; WO 93/10218. Within various embodiments, either the viral vector itself or a viral particle which contains the viral vector may be utilized in the methods and compositions described below.

Mammalian cells suitable for carrying out the present invention include, among others: PC12 (ATCC No. CRL1721), N1E-115 neuroblastoma, SK-N-BE(2)C neuroblastoma, SHSY5 adrenergic neuroblastoma, NS20Y and NG108-15 murine cholinergic cell lines, or rat F2 dorsal root ganglion line, COS (e.g., ATCC No. CRL 1650 or 1651), BHK (e.g., ATCC No. CRL 6281; BHK 570 cell line (deposited with the American Type Culture Collection under accession number CRL 10314), CHO (ATCC No. CCL 61), HeLa (e.g., ATCC No. CCL 2), 293 (ATCC No. 1573; Graham et al., *J. Gen. Virol.* 36:59–72, 1977) and NS-1 cells. Other mammalian cell lines may be used within the present invention, including Rat Hep I (ATCC No. CRL 1600), Rat Hep II (ATCC No. CRL 1548), TCMK (ATCC No. CCL 139), Human lung (ATCC No. CCL 75.1), Human hepatoma (ATCC No. HTB-52), Hep G2 (ATCC No. HB 8065), Mouse liver (ATCC No. CCL 29.1), NCTC 1469 (ATCC No. CCL 9.1), SP2/0-Ag14 (ATCC No. 1581), HIT-T15 (ATCC No. CRL 1777), and RINm 5AHT2B (Orskov and Nielson, *FEBS* 229(1):175–178, 1988).

Mammalian expression vectors for use in carrying out the present invention include a promoter capable of directing the transcription of a cloned gene or cDNA. Preferred promoters include viral promoters and cellular promoters. Viral promoters include the cytomegalovirus immediate early promoter (Boshart et al., *Cell* 41:521–530, 1985), cytomegalovirus immediate late promoter, SV40 promoter (Subramani et al., *Mol. Cell. Biol.* 1:854–864, 1981), MMTV LTR, RSV LTR, metallothionein-1, adenovirus E1a. Cellular promoters include the mouse metallothionein-1 promoter (Palmiter et al., U.S. Pat. No. 4,579,821), action promoters, a mouse $V_H$ promoter (Bergman et al., *Proc. Natl. Acad. Sci. USA* 81:7041–7045, 1983; Grant et al., *Nucl. Acids Res.* 15:5496, 1987) and a mouse $V_H$ promoter (Loh et al., *Cell* 33:85–93, 1983). The choice of promoter will depend, at least in part, upon the level of expression desired or the recipient cell line to be transfected.

Such expression vectors can also contain a set of RNA splice sites located downstream from the promoter and upstream from the DNA sequence encoding the peptide or protein of interest. Preferred RNA splice sites may be obtained from adenovirus and/or immunoglobulin genes. Also contained in the expression vectors is a polyadenylation signal located downstream of the coding sequence of interest. Suitable polyadenylation signals include the early or late polyadenylation signals from SV40 (Kaufman and Sharp, ibid.), the polyadenylation signal from the Adenovirus 5 E1B region and the human growth hormone gene terminator (DeNoto et al., *Nuc. Acids Res.* 9:3719–3730, 1981). The expression vectors may include a noncoding viral leader sequence, such as the Adenovirus 2 tripartite leader, located between the promoter and the RNA splice sites. Preferred vectors may also include enhancer sequences, such as the SV40 enhancer. Expression vectors may also include sequences encoding the adenovirus VA RNAs. Suitable expression vectors can be obtained from commercial sources (e.g., Stratagene, La Jolla, Calif.).

Vector constructs comprising isolated spa sequences can be introduced into cultured mammalian cells by, for example, calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841–845, 1982), or DEAE-dextran mediated transfection (Ausubel et al. (eds.), *Current Protocols in Molecular Biology*, John Wiley and Sons, Inc., NY, 1987). See generally Sambrook et al. (supra). To identify cells that have stably integrated the cloned DNA, a selectable marker is generally introduced into the cells along with the gene or cDNA of interest. Preferred selectable markers for use in cultured mammalian cells include genes that confer resistance to drugs, such as neomycin, hygromycin, and methotrexate. The selectable marker may be an amplifiable selectable marker. Preferred amplifiable selectable markers are the DHFR gene and the neomycin resistance gene. Selectable markers are reviewed by Thilly (*Mammalian Cell Technology*, Butterworth Publishers, Stoneham, Mass.).

Mammalian cells containing a suitable vector are allowed to grow for a period of time, typically 1–2 days, to begin expressing the DNA sequence(s) of interest. Drug selection is then applied to select for growth of cells that are expressing the selectable marker in a stable fashion. For cells that have been transfected with an amplifiable, selectable marker the drug concentration may be increased in a stepwise manner to select for increased copy number of the cloned sequences, thereby increasing expression levels. Cells expressing the introduced sequences are selected and screened for production of the protein of interest in the desired form or at the desired level. Cells that satisfy these criteria can then be cloned and scaled up for production.

Numerous insect host cells known in the art can also be useful within the present invention, in light of the subject specification. For example, the use of baculoviruses as vectors for expressing heterologous DNA sequences in insect cells has been reviewed by Atkinson et al. (*Pestic. Sci.* 28:215–224,1990).

Numerous plant host cells known in the art can also be useful within the present invention, in light of the subject specification. For example, the use of *Agrobacterium rhizogenes* as vectors for expressing genes in plant cells has been reviewed by Sinkar et al., *J. Biosci.* (*Bangalore*) 11:47–58, 1987.

Upon expression of the Spa polypeptides or fragments thereof in the host cells, the polypeptide or peptide may be preliminarily released and/or isolated from the host cell utilizing methods such as those discussed previously herein.

As noted above, depending on the host cell in which one desires to express a Spa polypeptide, an isolated nucleic acid encoding the polypeptide is introduced into an expression vector comprising a promoter that is active in the host cell. Other components of the expression unit such as transcribed but not translated sequences at the ends of the coding region may also be selected according to the particular host utilized. In some cases, it may be necessary to introduce artificially an intervening sequence to ensure high level expression. Expression can be monitored by SDS-PAGE and staining, if expression levels are sufficiently high. Additionally, if the protein is produced with a tag, detection by anti-tag antibody can be carried out and if produced with no tag, detection by anti-Spa antibody that does not recognize homologous proteins of the host may be employed. Further, any method known in the art for protein identification may be utilized to this end (e.g., a high resolution electrophoretic method or 2D electrophoresis).

III. Antibodies

In another aspect, the proteins of the present invention are utilized to prepare antibodies that specifically bind to an epitope present on Spa polypeptides Accordingly, the present invention also provides such antibodies. In preferred embodiments the antibodies bind to specific opsonic epitopes present on a Spa polypeptide. In a typical embodiment, the antibodies do not bind to epitopes present on M-proteins of a *Streptococcus* species. Within the context of the present invention, the term "antibodies" includes polyclonal antibodies, monoclonal antibodies, anti-idiotypic antibodies, fragments thereof such as F(ab')$_2$ and Fab fragments, and recombinantly or synthetically produced antibodies. Such antibodies incorporate the variable regions that permit a monoclonal antibody to specifically bind, which means an antibody able to selectively bind to a peptide produced from a spa gene of this invention. The affinity of a monoclonal antibody or antibody can be readily determined by one of ordinary skill in the art (see Scatchard, *Ann. N.Y. Acad. Sci.* 51:660–672, 1949).

Polyclonal antibodies can be readily generated by one of ordinary skill in the art from a variety of warm-blooded animals such as horses, cows, goats, sheep, dogs, chickens, turkeys, rabbits, mice, or rats. Briefly, the desired protein or peptide is utilized to immunize the animal through intraperitoneal, intramuscular, intraocular, or subcutaneous injections. The immunogenicity of the protein or peptide of interest may be increased through the use of an adjuvant such as Freund's complete or incomplete adjuvant. Following several booster immunizations, small samples of serum are collected and tested for reactivity to the desired protein or peptide.

Particularly preferred polyclonal antisera give a signal that is at least three times greater than background. Once the titer of the animal has reached a plateau in terms of its reactivity to the protein, larger quantities of polyclonal antisera may be readily obtained either by weekly bleedings, or by exsanguinating the animal.

Monoclonal antibodies can also be readily generated using well-known techniques (see U.S. Pat. Nos. RE 32,011, 4,902,614, 4,543,439, and 4,411,993; see also *Monoclonal Antibodies, Hybridomas: A New Dimension in Biological Analyses*, Plenum Press, Kennett, McKearn, and Bechtol (eds.), 1980, and *Antibodies: A Laboratory Manual*, Harlow and Lane (eds.), Cold Spring Harbor Laboratory Press, 1988). Briefly, in one embodiment, a subject animal such as a rat or mouse is injected with a desired protein or peptide. If desired, various techniques may be utilized in order to increase the resultant immune response generated by the protein, in order to develop greater antibody reactivity. For example, the desired protein or peptide may be coupled to another carrier protein such as ovalbumin or keyhole limpet hemocyanin (KLH), or through the use of adjuvants such as Freund's complete or incomplete adjuvant.

The present invention also provides fusion polypeptides or proteins containing a portion of a Spa polypeptide. Fusion proteins are useful for several purposes, including the combining of two or more catalytic functions from separate polypeptide sources, and for raising antibodies to epitopes. For raising antibodies to epitopes, the fusion protein typically contains a peptide epitope of a Spa of at least 8, 10, 15 or 20 amino acids fused to a protein that enhances an immune response to the epitope. A typical protein for this purpose is KLH. Therefore, another aspect of the present invention provides a non-naturally occurring fusion protein, comprising a first Spa polypeptide segment comprised of at least 8 contiguous amino acids of a Spa polypeptide or variant described above, fused in-frame to a second polypeptide segment. More preferred embodiments include Spa polypeptide segments of at least 10, 15 or 20 amino acids. The second polypeptide segment may optionally comprise another portion of the Spa polypeptide that is not naturally adjacent to the first segment, or comprise sequences from a non-Spa polypeptide. Also provided are nucleic acids and vectors encoding the aforementioned fusion proteins and host cells carrying the same.

Use of carrier proteins, fusion proteins or linkers is particularly advantageous when antibody is to be raised against a peptide antigen carrying an opsonic epitope One example of coupling to a carrier protein is shown in Example 5 where a synthetic 23 amino acid peptide comprising an N-terminus of a Spa polypeptides was linked to KLH in order to produces antibodies against an opsonic epitope contained within the peptide. Other suitable carrier proteins include but are not limited to tetanus toxoid, diphtheria toxoid, bovine serum albumin, hen egg lysozyme, gelatin, bovine gamma globulin, B subunit of cholera toxin, B subunit of *E. coli* labile toxin, and flagellin polymer. Typically, linking a Spa epitope to a carrier protein will usually include an in frame fusion of the peptide through a linker amino acid sequence of at least 2 amino acids in length. More typically the linker is 7 to 35 amino acids, and most typically about 7 to 15 amino acids wherein 2 to 7 of the linker amino acids are hydrophobic amino acids. The initial elicitation of an immune response may preferably be through intraperitoneal, intramuscular, intranasal, oral, or subcutaneous routes.

Between one and three weeks after the initial immunization, the animal may be reimmunized. The animal may then be test bled and the serum tested for binding to the desired antigen using assays as described above. Additional immunizations may also be accomplished until the animal has reached a plateau in its reactivity to the desired protein or peptide. The animal may then be given a final boost of the desired protein or peptide, and three to four days later sacrificed. At this time, the spleen and lymph nodes may be harvested and disrupted into a single cell suspension by passing the organs through a mesh screen or by rupturing the spleen or lymph node membranes which encapsulate the cells. Within one embodiment the red cells are subsequently lysed by the addition of a hypotonic solution, followed by immediate return to isotonicity.

Within another embodiment, suitable cells for preparing monoclonal antibodies are obtained through the use of in vitro immunization techniques. Briefly, an animal is sacrificed, and the spleen and lymph node cells are removed as described above. A single cell suspension is prepared, and the cells are placed into a culture containing a form of the protein or peptide of interest that is suitable for generating an immune response as described above. Subsequently, the lymphocytes are harvested and fused as described below.

Cells that are obtained through the use of in vitro immunization or from an immunized animal as described above may be immortalized by transfection with a virus such as the Epstein-Barr Virus (EBV). (See Glasky and Reading, *Hybridoma* 8(4):377–389, 1989.) Alternatively, within a preferred embodiment, the harvested spleen and/or lymph node cell suspensions are fused with a suitable myeloma cell in order to create a "hybridoma" which secretes monoclonal antibodies. Suitable myeloma lines are preferably defective in the construction or expression of antibodies, and are additionally syngeneic with the cells from the immunized animal. Many such myeloma cell lines are well known in the art and may be obtained from sources such as the American Type Culture Collection (ATCC), Manassas, Va. (see *Catalogue of Cell Lines & Hybridomas*, $6^{th}$ ed., ATCC, 1988). Representative myeloma lines include: for humans, UC 729-6 (ATCC No. CRL 8061), MC/CAR-Z2 (ATCC No. CRL 8147), and SKO-007 (ATCC No. CRL 8033); for mice, SP2/0-Ag14 (ATCC No. CRL 1581), and P3X63Ag8 (ATCC No. TIB 9); and for rats, Y3-Ag1.2.3 (ATCC No. CRL 1631), and YB2/0 (ATCC No. CRL 1662). Particularly preferred fusion lines include NS-1 (ATCC No. TIB 18) and P3X63-Ag 8.653 (ATCC No. CRL 1580), which may be utilized for fusions with either mouse, rat, or human cell lines. Fusion between the myeloma cell line and the cells from the immunized animal can be accomplished by a variety of methods, including the use of polyethylene glycol (PEG) (see *Antibodies: A Laboratory Manual*, Harlow and Lane, supra) or electrofusion. (See Zimmerman and Vienken, *J. Membrane Biol.* 67:165–182, 1982.)

Following the fusion, the cells are placed into culture plates containing a suitable medium, such as RPMI 1640 or DMEM (Dulbecco's Modified Eagles Medium, JRH Biosciences, Lenexa, Kan.). The medium may also contain additional ingredients, such as Fetal Bovine Serum (FBS, e.g., from Hyclone, Logan, Utah, or JRH Biosciences), thymocytes that were harvested from a baby animal of the same species as was used for immunization, or agar to solidify the medium. Additionally, the medium should contain a reagent which selectively allows for the growth of fused spleen and myeloma cells. Particularly preferred is the use of HAT medium (hypoxanthine, aminopterin, and thymidine) (Sigma Chemical Co., St. Louis, Mo.). After about seven days, the resulting fused cells or hybridomas may be screened in order to determine the presence of antibodies which recognize the desired antigen. Following several clonal dilutions and reassays, hybridoma producing antibodies that bind to the protein of interest can be isolated.

Other techniques may also be utilized to construct monoclonal antibodies. (See Huse et al., "Generation of a Large Combinational Library of the Immunoglobulin Repertoire in Phage Lambda," *Science* 246:1275–1281, 1989; see also Sastry et al., "Cloning of the Immunological Repertoire in *Escherichia coli* for Generation of Monoclonal Catalytic Antibodies: Construction of a Heavy Chain Variable Region-Specific cDNA Library," *Proc. Natl. Acad. Sci. USA* 86:5728–5732, 1989; see also Alting-Mees et al., "Monoclonal Antibody Expression Libraries: A Rapid Alternative to Hybridomas," *Strategies in Molecular Biology* 3:1–9, 1990; these references describe a commercial system available from Stratagene, La Jolla, Calif., which enables the production of antibodies through recombinant techniques.) Briefly, mRNA is isolated from a B cell population and utilized to create heavy and light chain immunoglobulin cDNA expression libraries in the λIMMUNOZAP(H) and λIMMUNOZAP(L) vectors. These vectors may be screened individually or co-expressed to form Fab fragments or antibodies (see Huse et al. (supra); see also Sastry et al. (supra)). Positive plaques can subsequently be converted to a non-lytic plasmid which allows high level expression of monoclonal antibody fragments from *E. coli*.

Similarly, antibodies can also be constructed utilizing recombinant DNA techniques to incorporate the variable regions of a gene that encodes a specifically binding antibody. The construction of these antibodies can be readily accomplished by one of ordinary skill in the art given the disclosure provided herein. (See Larrick et al., "Polymerase Chain Reaction Using Mixed Primers: Cloning of Human Monoclonal Antibody Variable Region Genes From Single Hybridoma Cells," *Biotechnology* 7:934–938, 1989; Riechmann et al., "Reshaping Human Antibodies for Therapy," *Nature* 332:323–327, 1988; Roberts et al., "Generation of an Antibody with Enhanced Affinity and Specificity for its Antigen by Protein Engineering," *Nature* 328:731–734, 1987; Verhoeyen et al., "Reshaping Human Antibodies: Grafting an Antilysozyme Activity," *Science* 239:1534–1536, 1988; Chaudhary et al., "A Recombinant Immunotoxin Consisting of Two Antibody Variable Domains Fused to *Pseudomonas* Exotoxin," *Nature* 339: 394–397, 1989; see also U.S. Pat. No. 5,132,405 entitled "Biosynthetic Antibody Binding Sites.") Briefly, in one embodiment, DNA segments encoding the desired protein or peptide of interest-specific antigen binding domains are amplified from hybridomas that produce a specifically binding monoclonal antibody, and are inserted directly into the genome of a cell that produces human antibodies. (See Verhoeyen et al. (supra); see also Reichmann et al. (supra)). This technique allows the antigen-binding site of a specifically binding mouse or rat monoclonal antibody to be transferred into a human antibody. Such antibodies are preferable for therapeutic use in humans because they are not as antigenic as rat or mouse antibodies.

In an alternative embodiment, genes that encode the variable region from a hybridoma producing a monoclonal antibody of interest are amplified using oligonucleotide primers for the variable region. These primers may be synthesized by one of ordinary skill in the art, or may be purchased from commercially available sources. For instance, primers for mouse and human variable regions including, among others, primers for $V_{Ha}$, $V_{Hb}$, $V_{Hc}$, $V_{Hd}$, $C_{H1}$, $V_L$ and $C_L$ regions, are available from Stratagene (La Jolla, Calif.). These primers may be utilized to amplify heavy or light chain variable regions, which may then be inserted into vectors such as IMMUNOZAP™(H) or IMMUNOZAP™(L) (Stratagene), respectively. These vectors may then be introduced into *E. coli* for expression. Utilizing these techniques, large amounts of a single-chain polypeptide containing a fusion of the $V_H$ and $V_L$ domains may be produced (see Bird et al., *Science* 242:423–426, 1988).

Monoclonal antibodies and other antibodies can be produced in a number of host systems, including tissue cultures, bacteria, eukaryotic cells, plants and other host systems known in the art.

Once suitable antibodies or antibodies have been obtained, they may be isolated or purified by many techniques well known to those of ordinary skill in the art (see *Antibodies: A Laboratory Manual*, Harlow and Lane (supra)). Suitable techniques include peptide or protein affinity columns, HPLC or RP-HPLC, purification on protein A or protein G columns, or any combination of these techniques. Within the context of the present invention, the term "isolated" as used to define antibodies or antibodies means "substantially free of other blood components."

The antibodies of the present invention have many uses. For example, antibodies can be utilized in flow cytometry to identify cells bearing such a protein. Briefly, in order to detect the protein or peptide of interest on cells, the cells are incubated with a labeled monoclonal antibody which specifically binds to the protein of interest, followed by detection of the presence of bound antibody. Labels suitable for use within the present invention are well known in the art including, among others, flourescein isothiocyanate (FITC), phycoerythrin (PE), horse radish peroxidase (HRP), and colloidal gold. Particularly preferred for use in flow cytometry is FITC, which may be conjugated to purified antibody according to the method of Keltkamp in "Conjugation of Fluorescein Isothiocyanate to Antibodies. I. Experiments on the Conditions of Conjugation," *Immunology* 18:865–873, 1970. (See also Keltkamp, "Conjugation of Fluorescein Isothiocyanate to Antibodies. II. A Reproducible Method," *Immunology* 18:875–881, 1970; Goding, "Conjugation of Antibodies with Fluorochromes: Modification to the Standard Methods," *J. Immunol. Methods* 13:215–226, 1970.) The antibodies can also be used to target drugs against Streptococci, to diagnose infection by these bacteria, or for treating an infection caused thereby.

IV. Diagnostic Application of Spa Nucleotide Sequences

Nucleic acid molecules can be used to detect the expression of the spa gene in a biological sample. Such probe molecules include double-stranded nucleic acid molecules comprising the nucleotide sequence of SEQ ID NOS:1 or 4 or a fragment thereof, as well as single-stranded nucleic acid molecules having the complement of the nucleotide sequence of SEQ ID NOS:1 or 4 or a fragment thereof. Probe molecules may be DNA, RNA, oligonucleotides, and the like.

Preferred probes bind with regions of the spa gene that have a low sequence similarity to comparable regions in other Streptococcal proteins. For example, suitable probes will bind with at least one portion of the nucleotide sequence of SEQ ID NO:1. As used herein, the term "portion" refers to at least eight or more nucleotides.

In a basic assay, a single-stranded probe molecule is incubated with RNA, isolated from a biological sample, under conditions of temperature and ionic strength that promote base pairing between the probe and target Spa RNA species. After separating unbound probe from hybridized molecules, the amount of hybrids is detected.

Well-established hybridization methods of RNA detection include northern analysis and dot/slot blot hybridization (see, for example, Ausubel (1995) at pages 4-1 to 4-27, and Wu et al. (eds.), "Analysis of Gene Expression at the RNA Level," in *Methods in Gene Biotechnology*, pages 225–239 (CRC Press, Inc. 1997)). Nucleic acid probes can be detectably labeled with radioisotopes such as $^{32}P$ or $^{35}S$. Alternatively, Spa RNA can be detected with a nonradioactive hybridization method (see, for example, Isaac (ed.), *Protocols for Nucleic Acid Analysis by Nonradioactive Probes* (Humana Press, Inc. 1993)). Typically, nonradioactive detection is achieved by enzymatic conversion of chromogenic or chemiluminescent substrates. Illustrative nonradioactive moieties include biotin, fluorescein, and digoxigenin.

Numerous diagnostic procedures take advantage of the polymerase chain reaction (PCR) to increase sensitivity of detection methods. Standard techniques for performing PCR are well-known (see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

Preferably, PCR primers are designed to amplify a portion of the spa gene that has a low sequence similarity to other Streptococcal proteins. As an illustration, primers having the nucleotide sequences of SEQ. ID NOS: 6 and 7 are suitable for amplifying a spa gene from several Streptococci. In addition suitable primers include those designed to amplify portions of a spa gene encoding an immunogenic epitope of SEQ ID NOS: 2 or 5.

One variation of PCR for diagnostic assays is reverse transcriptase-PCR (RT-PCR). RT-PCR has been used to detect dissemination of prostate cancer cells to metastatic sites in prostate cancer patients (Moreno et al., *Cancer Res.* 52:6110, 1992; Vessella et al., *Proc. Am. Assoc. Can. Res.* 33:2367, 1992; Olsson et al., *Urologic Clinics of North America* 24:367 (1997); Robbins, International Publication No. WO 97/39139). In the RT-PCR technique, RNA is isolated from a biological sample, reverse transcribed to cDNA, and the cDNA is incubated with Spa primers (see, for example, Wu et al. (eds.), "Rapid Isolation of Specific cDNAs or Genes by PCR," in *Methods in Gene Biotechnology*, pages 15–28 (CRC Press, Inc. 1997)). PCR is then performed and the products are analyzed using standard techniques.

Briefly, a biological sample is obtained from a sample for RNA preparation. If the test material contains a variety of biological materials, then the sample may be layered onto a Ficoll-Hypaque density gradient and centrifuged in order to separate some of the biological materials.

RNA may then be isolated from the sample using, for example, the gunadinium-thiocyanate cell lysis procedure described above. Alternatively, a solid-phase technique can be used to isolate mRNA from a cell lysate. A reverse transcription reaction can be primed with the isolated RNA using random oligonucleotides, short homopolymers of dT, or Spa antisense oligomers. Oligo-dT primers offer the advantage that various mRNA nucleotide sequences are amplified that can provide control target sequences. Spa sequences are amplified by the polymerase chain reaction using two flanking oligonucleotide primers that are typically 20 bases in length.

PCR amplification products can be detected using a variety of approaches. For example, PCR products can be fractionated by gel electrophoresis, and visualized by ethidium bromide staining. Alternatively, fractionated PCR products can be transferred to a membrane, hybridized with a detectably-labeled Spa probe, and examined by autoradiography. Additional alternative approaches include the use of digoxigenin-labeled deoxyribonucleic acid triphosphates to provide chemiluminescence detection, and the C-TRAK colorimetric assay.

Another approach for detection of Spa expression is cycling probe technology (CPT), in which a single-stranded DNA target binds with an excess of DNA-RNA-DNA chimeric probe to form a complex, the RNA portion is cleaved with RNAase H, and the presence of cleaved chimeric probe is detected (see, for example, Beggs et al., *J. Clin. Microbiol.* 34:2985, 1996, Bekkaoui et al., *Biotechniques* 20:240, 1996). Alternative methods for detection of Spa sequences can utilize approaches such as nucleic acid sequence-based amplification (NASBA), cooperative amplification of templates by cross-hybridization (CATCH), and the ligase chain reaction (LCR) (see, for example, Marshall et al., U.S. Pat. No. 5,686,272 (1997), Dyer et al., *J. Virol. Methods* 60:161, 1996, Ehricht et al., *Eur. J. Biochem.* 243:358, 1997, and Chadwick et al., *J. Virol. Methods* 70:59, 1998). Other standard methods are known to those of skill in the art.

Various additional diagnostic approaches are well-known to those of skill in the art (see, for example, Mathew (ed.), *Protocols in Human Molecular Genetics* (Humana Press, Inc. 1991), Coleman and Tsongalis, *Molecular Diagnostics* (Humana Press, Inc. 1996), and Elles, *Molecular Diagnosis of Genetic Diseases* (Humana Press, Inc., 1996)).

The present invention also contemplates kits for performing a diagnostic assay for spa gene expression. Such kits comprise nucleic acid probes comprising a portion of the nucleotide sequence of SEQ ID NOS:1 or 4, or a fragment thereof, or nucleic acids encoding a peptide according to SEQ. ID NOS: 2, 3 or 5 or fragments thereof. Probe molecules may be DNA, RNA, oligonucleotides, and the like. Kits may comprise nucleic acid primers for performing PCR.

Preferably, such a kit contains all the necessary elements to perform a nucleic acid diagnostic assay described above. A kit will comprise one or more containers, in which one container comprises a Spa probe or primer, and a second container comprises one or more reagents capable of indicating the presence of Spa sequences. Examples of such indicator reagents include detectable labels such as radioactive labels, fluorochromes, chemiluminescent agents, and the like. A kit will also comprise written material describing the use of such Spa probes and primers for detection of spa gene expression. The written material can be applied directly to a container, or the written material can be provided in the form of a packaging insert.

V. Diagnostic Application of Anti-Spa Antibodies

The present invention further contemplates the use of anti-Spa antibodies to screen biological samples in vitro for the presence of Spa. In one type of in vitro assay, anti-Spa antibodies are used in liquid phase. For example, the presence of Spa in a biological sample can be tested by mixing the biological sample with a trace amount of labeled Spa and an anti-Spa antibody under conditions that promote binding between Spa and its antibody. Complexes of Spa and anti-Spa in the sample can be separated from the reaction mixture by contacting the complex with an immobilized protein which binds with the antibody, such as an Fc antibody or *Staphylococcus* protein A. The concentration of Spa in the biological sample will be inversely proportional to the amount of labeled Spa bound to the antibody and directly related to the amount of free labeled Spa.

Alternatively, in vitro assays can be performed in which anti-Spa antibody is bound to a solid-phase carrier. For example, antibody can be attached to a polymer, such as aminodextran, in order to link the antibody to an insoluble support such as a polymer-coated bead, a plate or a tube. Other suitable in vitro assays will be readily apparent to those of skill in the art.

Immunochemical detection can be performed by contacting a biological sample with an anti-Spa antibody, and then contacting the biological sample with a detectably labeled molecule which binds to the antibody. For example, the detectably labeled molecule can comprise an antibody moiety that binds to anti-Spa antibody. Alternatively, the anti-Spa antibody can be conjugated with avidin/streptavidin (or biotin) and the detectably labeled molecule can comprise biotin (or avidin/streptavidin). Numerous variations of this basic technique are well-known to those of skill in the art.

Alternatively, an anti-Spa antibody can be conjugated with a detectable label to form an anti-Spa immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3$H, $^{125}$I, $^{131}$I, $^{35}$S and $^{14}$C.

Anti-Spa immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-Spa immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-Spa immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-Spa immunoconjugates can be detectably labeled by linking an anti-Spa antibody component to an enzyme. When the anti-Spa-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-Spa antibodies can be accomplished using standard techniques known to the art. Typical methodology in this regard is described by Kennedy et al., *Clin. Chim. Acta* 70:1, 1976, Schurs et al., *Clin. Chim. Acta* 81:1, 1977, Shih et al., *Int'l J. Cancer* 46:1101, 1990, Stein et al., *Cancer Res.* 50:1330, 1990), and Coligan, supra.

Moreover, the convenience and versatility of immunochemical detection can be enhanced by using anti-Spa antibodies that have been conjugated with avidin, streptavidin, and biotin (see, for example, Wilchek et al. (eds.), "Avidin-Biotin Technology," *Methods In Enzymology, Vol.* 184 (Academic Press 1990), and Bayer et al., "Immunochemical Applications of Avidin-Biotin Technology," in *Methods In Molecular Biology, Vol.* 10, Manson (ed.), pages 149–162 (The Humana Press, Inc. 1992).

Methods for performing immunoassays are well-established (see, for example, Cook and Self, "Monoclonal Antibodies in Diagnostic Immunoassays," in *Monoclonal Antibodies: Production, Engineering, and Clinical Application*, Ritter and Ladyman (eds.), pages 180–208, (Cambridge University Press, 1995), Perry, "The Role of Monoclonal Antibodies in the Advancement of Immunoassay Technology," in *Monoclonal Antibodies: Principles and Applications*, Birch and Lennox (eds.), pages 107–120 (Wiley-Liss, Inc. 1995), and Diamandis, *Immunoassay* (Academic Press, Inc. 1996)).

The present invention also contemplates kits for performing an immunological diagnostic assay for spa genes. Such kits comprise one or more containers, in which one container comprises an anti-Spa antibody, or antibody fragment. A second container may comprise one or more reagents capable of indicating the presence of Spa antibody or antibody fragments. Examples of such indicator reagents include detectable labels such as a radioactive label, a fluorescent label, a chemiluminescent label, an enzyme label, a bioluminescent label, colloidal gold, and the like. A kit will also comprise written material describing the use of Spa antibodies and antibody fragments for detection of Spa protein. The written material can be applied directly to a container, or the written material can be provided in the form of a packaging insert.

VI. Therapeutic Compositions.

The discovery of a new protective antigen of group A Streptococci enables another aspect of this invention which is the provision of therapeutic compositions to protect against infections caused by group A Streptococci. As use herein to "protect against infections" means to prevent, reduce the likelihood of, or ameliorate the pathogenic effects of, an infection caused by a *Streptococcus* In one embodiment, isolated Spa antigens of the this invention are formulated in a therapeutically suitable medium and used to elicit cross-protective antibodies in an animal. Spa antigens include the aforementioned proteins, polypeptides or peptides whether naturally occurring, synthetic, or produced by expression of a recombinant DNA vector containing a nucleic acid sequence encoding a Spa antigen, which are reactive with antibodies raised against the purified Spa protein or peptides of the present invention.

In a typical embodiment, the therapeutic composition containing a Spa antigen comprises an antigen that is protective against a multiple Streptococci serotypes. In a more typical embodiment the therapeutic composition contains an opsonic epitope that is cross protective against group A Streptococci including Type 28, Type 3, Type 18 Streptococci. Such a composition is expected to be considerably less complex than previous compositions comprised of M-protein or derivative thereof, for example, compositions where limited amino-terminal fragments of different M proteins are linked in tandem to evoke protective immune responses against each serotype represented in the vaccine. While such an approach has the advantage of limiting the amount of M protein contained in a vaccine, a large number of combinations must be provided because each M protein fragment is type-specific. This necessitates the development of relatively complex vaccines to prevent the majority of Streptococcal infections in a given population or geographic region. In contrast, the Spa antigens and antibodies, and nucleic acids of the present invention can be used to provide broad protection and/or can be used in combination with M-proteins and peptides to enhance the effectiveness of protection provided by either protein alone.

In this aspect, the present invention provides compositions and methods comprising one or more of the above-described Spa antigens or antibodies thereto in combination with one or more pharmaceutically or physiologically acceptable carriers, adjuvants, binders or diluents. Compositions containing antigens can be used to elicit or enhance an immune response in a recipient animal, which is preferably a human being, and preferably elicits or enhances a protective or partially protective immunity against *Streptococcus*, or against a host cell expressing a surface antigen comprised of a Spa antigen of the present invention. Compositions containing antibodies may be used to diagnose or treat infections caused by Streptococci.

Preferably, such carriers, adjuvants, binders or diluents are nontoxic to recipients at the dosages and concentrations employed. Ordinarily, the preparation of such compositions entails combining the an antigen or antibody of this invention with buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Examples of adjuvants include alum or aluminum hydroxide for humans.

It will be evident in light of the present specification to those in the art that the amount and frequency of administration can be optimized in clinical trials, and will depend upon such factors as the disease or disorder to be treated, the degree of immune inducement, enhancement, or protection required, and many other factors.

In one embodiment, the therapeutic composition is administered orally, and a Spa antigen of the invention is taken up by cells, such as cells located in the lumen of the gut. Alternatively, the therapeutic composition can be parenterally administered via the subcutaneous route, or via other parenteral routes. Other routes include buccal/sublingual, rectal, nasal, topical (such as transdermal and ophthalmic), vaginal, pulmonary, intraarterial, intramuscular, intraperitoneal, intraocular, intranasal or intravenous, or indirectly. The Spa compositions of the present invention can be prepared and administered as a liquid solution, or prepared as a solid form (e.g., lyophilized) which can be administered in solid form or resuspended in a solution in conjunction with administration.

Depending upon the application, quantities of Spa antigen in the composition will vary generally from about 0.1 μg to 1000 mg, typically from about 1 μg to 100 mg, more typically from about 10 μg to 10 mg, and usually from about 100 μg to 1 mg, in combination with the physiologically acceptable carrier, binder or diluent. Booster immunizations can be given at 2–6 weeks intervals.

The Spa antigens of this invention may also be used with immunological carriers in conjugate vaccines. Preferably, a beneficial carrier includes another polypeptide that is has immunostimulent but does not have immunosuppressive effects. Such carriers may be used to elicit an increased immune response to the conjugated molecule. The spa gene products of this invention may also be used as carriers (in conjugates or fusion proteins) in combination with other antigens so as to provide compositions providing further protection elicited by epitopes additional to those contained on Spa, for example, M protein polypeptides may.

A further aspect of the present invention is protection from *Streptococcus* infections by treatment of an animal, preferably an animal and most preferably a human with a therapeutic composition containing the Spa antigens or antibodies of the present invention. As used herein, "protection" means to prevent or to reduce the severity of a disease associated with a *Streptococcus* infection. In a typical practice, the Spa antigens of the present invention provide protection against multiple serotypes of Streptococci. In one embodiment, protection is provided against multiple stereotypes of group A Streptococci. The capacity for protection against multiple serotypes is illustrated for example in Table 5 (Example 6) where it is shown that a composition comprised of crude surface peptides containing a Spa polypeptide or an isolated Spa polypeptide from a Type 18 Streptococci elicited production of antisera that provided opsonic protection against Type 3, Type 18 and Type 28 Streptococci. In addition, Tables 3 and 4 (Example 5) show that antisera raised against the 23 amino acid N terminus of a Spa polypeptide displayed similar opsonization and bactericidal activity TO antisera against the crude peptides and isolated Spa polypeptides.

VII. Therapeutic Methods

Accordingly, another aspect of the present invention is therapeutic methods for protecting an animal against a *Streptococcus* infection that includes the step of administering to the animal at least one of the aforementioned therapeutic compositions. Typically, administering a therapeutic compositions containing Spa antigens elicits opsonic antibodies in the animal. Similarly, administering a composition containing antibodies raised against Spa antigens will provide opsonic antibodies which facilitate a phagocytic responses in the animal. In a preferred embodiment, protection is provided against multiple serotypes of *Streptococcus*. In a related embodiment, the therapeutic composition is administered by at least one of oral administration, intranasal administration, intramuscular vaccination, subcutaneous vaccination, or vascular vaccination. In another preferred embodiment, the therapeutic method is used with the human.

The compositions and methodologies described herein are suitable for a variety of uses. To this end, the following examples are presented for purposes of illustration, not limitation.

EXAMPLES

Example 1

Construction and Characterization of an M-Negative Mutant (M18Ω)

Bacterial strains. The parent Type 18 Streptococcal strain 87-282, was obtained from Dr. P. Patrick Cleary at the University of Minnesota. The M3 strain (3375) was provided by Dr. James Musser, Baylor College of Medicine, Houston, Tex. The M28 strain (S2356) was from our laboratory collection.

The new Streptococcal protective antigen was discovered during studies of an M-negative mutant of Type 18 Streptococci. Briefly, as discussed in more detail below, the M-negative M18 strain was constructed by interrupting the emm18 gene with an Ω-element. Southern blot analyses of chromosomal DNA from the M18 and M18Ω strains that was probed with (Km2 and emm18 fragments and PCR analyses using primers from the emm gene and the Ω-element revealed that there was a single copy of the Ω-element inserted ~140 bp beyond the start codon of the emm18 gene.

A fragment of the emm18 gene was initially cloned by PCR using a forward primer that copied the 3' end of the emm18 gene and a reverse primer that was specific for this subfamily (SF 3) of emm-like genes. The purified PCR product was ligated into pKK223-3 and the insert was sequenced by standard methods. The intact emm18 gene was later cloned using a reverse primer that copied the 5' end of the scpA gene and the purified PCR product was ligated into pQE-30 (Qiagen, Chatsworth, Calif.). The recombinant Emm18 protein was purified by affinity chromatography over a nickel column according to the instructions provided by Qiagen.

Insertion of the Ω-interposon into emm18 and transformation of Type 18 Streptococci was accomplished essentially as previously described for Type 24 Streptococci. Briefly, emm18 was ligated into pKK223-3 and then cut with XhoI, which recognizes a single site between bases 136 and 141 of the emm18 gene. The ends were repaired with Klenow fragment. Plasmid pBR322-Ω,Km2 was digested with SmaI and the Ω,Km2 fragment was purified from a 0.8% agarose gel and ligated into the cut emm18 gene. The resulting plasmid, pKKM18Ω, was electroporated into Type 18 Streptococci. One kanamycin-resistant colony, designated M18Ω, was selected for further study.

To confirm that the emm18 gene was not expressed in the M18Ω strain, immunoblots were performed using extracts of whole bacteria and rabbit antisera evoked by purified recombinant M18 (rM18), a synthetic peptide of M18, SM18(1–30), and a synthetic peptide SM5(265–291), which copies the C-repeat domain of Type 5 M protein that is common to all M proteins (FIG. 1). Anti-rM18 reacted with a triplet of proteins extracted from the parent strain, the largest of which had an apparent M.W. of ~43 kDa (FIG. 1, lane A). The immunoreactive proteins with lower M.W. are presumably degradation products of M18 that were present in the crude extracts of whole bacteria. There was no reaction of rM18 antiserum with the extract from the M18Ω mutant (FIG. 1, lane B). Anti-SM18(1–30) reacted only with proteins in extracts from the parent strain (FIG. 1, lane C) and the pattern was identical to that observed with antiserum against rM18. Interestingly, antiserum against the C-repeat peptide of M protein, SM5(265–291), reacted only with an extract from the parent strain (FIG. 1, lane E) and not with an extract from the mutant (lane F), suggesting that the mutant did not express another M or M-like protein containing these shared repeating epitopes. These data, taken together with the results of the Southern blots and PCR, indicate that the Ω element was inserted in the emm18 gene and the M18 protein was not expressed by M18Ω.

Western blots were performed using extracts of intact Streptococci and purified proteins as previously described In some experiments using purified recombinant Emm18 protein, the nitrocellulose membranes were first incubated in buffer containing 10% normal human serum to block non-specific binding of immunoglobulins.

For southern blots, Streptococcal chromosomal DNA was digested with BsaH I and electrophoresed in a 1% agarose gel. The DNA fragments were transferred to a nylon membrane (Sigma) and probed with digoxigenin-labeled (Km2 fragment or emm18 according to instructions provided by the manufacturer (Boehringer Mannheim, Indianapolis, Ind.).

Example 2

Growth in Blood and Mouse Virulence of M18 and M18Ω

A. Growth in non-immune human blood. The virulence of the M-negative mutant of Type 18 Streptococci was first assessed by its ability to grow in nonimmune human blood (Table 1). Streptococci were grown to early log-phase in Todd-Hewitt broth and the inoculum indicated was added to 0.45 ml normal, heparinized human blood that did not contain M18 antibodies. The mixture was rotated end-over-end at 37° C. for 3 hr. Organisms surviving were quantitated on pour plates of sheep's blood agar using an aliquot of the mixture. The parent strain of M18 grew to just over 8 generations after a three-hour rotation in blood. The M18Ω mutant grew to approximately 7.5 generations in the same assay.

TABLE 1

Growth in human blood of M18 and M18Ω *Streptococci*.

| Organism | CFU surviving 3 hr rotation (# of generations) | |
|---|---|---|
| M18 | inoculum: 45 12,550 (8.1) | inoculum: 15 4,800 (8.3) |
| M18Ω | inoculum: 55 9,940 (7.3) | inoculum: 20 4,210 (7.6) |

B. Intraperitoneal challenge infections. The most stringent laboratory assay for virulence is intraperitoneal challenge infections of nonimmune mice. Briefly, four groups of six Swiss white mice each were challenged with 10-fold increasing inocula, ranging from $2.7 \times 10^4$ to $2.7 \times 10^7$ CFU of either M18 or M18Ω. Deaths were recorded for seven days following challenge infections. The LD50 was determined by the method of Reed and Muench after using 10-fold increasing doses of each organism. The LD50 of the parent M18 strain was $0.73 \times 10^5$ and of the M18Ω was $1.26 \times 10^5$. Of 24 mice challenged with each organism, 8 challenged with M18 died while 7 challenged with M18Ω died. Organisms recovered from the spleens of mice that succumbed to challenge infections with M18Ω were kanamycin-resistant and M18 negative, indicating that there was no reversion to the parent phenotype in vivo. These results demonstrated that the expression of M18 was not required for virulence of Type 18 Streptococci.

Example 3

Opsonization of M18 and M18Ω Particles Using Antisera Against Crude Surface Peptides Interruption of emm18 expression could have resulted in a mutant that was virulent and did not express a protective antigen, or alternatively, one that expressed a second protective antigen on its surface. In order to assess the possibility of the latter, in vitro opsonization experiments were performed to determine whether M18Ω expressed a surface antigen that contained opsonic epitopes. Early log-phase cultures of Streptococci were added to 0.1 ml of test serum and incubated for 15 min. at ambient temperature. To this was added 0.4 ml of normal, heparinized human blood and the entire mixture was rotated end-over-end for 45 min. at 37° C. At the end of the rotation, a drop of each mixture was used to make thin smears on microscope slides. After staining the slides with Wright's stain, the percentage of neutrophils with associated Streptococci (either ingested or attached) was estimated by counting at least 50 consecutive neutrophils. Anti-rM18, rabbit antiserum against intact, recombinant Type 18 M protein; anti-SM18(1–30), rabbit antiserum against a synthetic peptide that copied the N-terminal 30 amino acids of M18 linked to KLH; anti-crude pep M18, rabbit antiserum against a partially purified pepsin extract of whole Type 18 Streptococci. Experiments were repeated at least three times with similar results.

The bactericidal activity of test antisera was determined using a similar assay except that fewer Streptococci were added to the mixture, which was rotated for 3 hr. at 37° C. At the end of the rotation, 0.1 ml aliquots were added to sheep blood agar and pour plates were made to quantitate viable bacteria. Results shown in Table 2 below are from one representative experiment. Briefly, only the M18 parent strain was opsonized by antisera against SM18(1–30) or recombinant M18. The association of M18Ω with PMNs remained at baseline levels in the presence of both of these antisera. Antiserum raised in rabbits against a crude pepsin extract of the M18Ω strain, however, opsonized both the parent and the M-negative mutant (Table 2). This antiserum was used in subsequent experiments to identify and purify the putative new protective antigen of Type 18 Streptococci.

TABLE 2

Opsonization of M18 and M18Ω by rabbit antisera against recombinant M18, S-M18(1–30), and crude pep M18.

| Antiserum | Percent neutrophils with associated *Streptococci* | |
|---|---|---|
| | M18 | M18Ω |
| Pre-pool | 2 | 8 |
| Anti-rM18 | 92 | 14 |
| Anti-SM18(1–30) | 98 | 8 |
| Anti-crude pep M18 | 96 | 88 |

Example 4

Identification, Purification, and Amino-Acid Sequence Anaylsis of Spa

As is discussed in more detail in the following example, peptide fragments from the surface of M18Ω were extracted using dilute solutions of pepsin at suboptimal pH. The extract was precipitated in 60% saturated ammonium sulfate, dialyzed extensively against distilled water, and then lyophilized. The mixture of surface proteins and peptides is referred to as crude pep M18Ω.

More specifically, as described above in Example 3, Spa was identified in the crude pepsin extract by opsonization inhibition assays. The crude pep M18Ω was separated by SDS-PAGE on a preparative 10% gel using reducing conditions. The entire gel was electroblotted to nitrocellulose paper and each end was cut vertically and stained with Coomassie® blue. The center section of the nitrocellulose paper was cut into horizontal strips approximately 8–10 mm in width. Each strip was then used to absorb rabbit antiserum raised against the crude pep M18Ω for 2 hours at 37° C. One section of the nitrocellulose paper was western blotted with pep M18Ω antiserum to identify immunoreactive bands. Another section was cut into horizontal strips that were used to absorb opsonic antibodies in the pep M18Ω antiserum. The pep M18Ω extract contained a protein with an apparent M.W. of 24 kDa (Spa) that absorbed the majority of the opsonic antibodies in the pep M18Ω antiserum (FIG. 2).

Opsonization assays were performed using absorbed serum samples and unabsorbed serum, as described above in Example 3. Once the opsonic-inhibitory peptide had been identified in the crude pepsin extract, it was purified by ammonium sulfate precipitation and preparative gel electrophoresis (Prep Cell, model 491, Bio-Rad, Richmond, Calif.).

The purified Spa migrated as a single band, as assessed by SDS-PAGE, with a M.W. of 24 kDa (FIG. 3, Lane B). The purified Spa protein was electrophoretically transferred to a PVDF membrane and submitted to the Protein and Nucleic Acid Facility, Beckman Center, Stanford University Medical Center for N-terminal sequencing by Edman degradation. The sequence of an internal peptide of Spa was also determined in the Stanford University Facility. The intact protein on PVDF was digested with LysC protease, 0.25 (mol/ml, at 37° C. overnight). The resultant peptides were purified by HPLC on a Vydac C18 column. Selected fractions were assessed for purity by mass spectroscopy and one peptide with a mass of 1249 Daltons was selected for N-terminal sequencing.

Edman degradation of the purified protein revealed the sequence of the first 23 amino acids (N-terminus) to be:
DSVSG LEVAD PSDSK KLIEL GLA (SEQ ID NO:3)

In addition, an internal peptide purified from a LysC digest of the purified Spa contained the amino-terminal sequence:
YRLDS ESHLK. (SEQ ID NO:8)

Example 5

Identification of Opsonic Epitopes of Spa

Rabbit antisera was prepared against the synthetic peptide SM18(1–30)C against recombinant M18, which was purified from periplasmic extracts of *E. coli*, and against purified Spa.

To directly assess the presence of bactericidal epitopes in Spa, rabbits were immunized with 100 μg of the purified protein in CFA at time 0, 4 weeks, and 8 weeks. Sera from all three immunized rabbits obtained 10 weeks after the first injection contained antibodies that opsonized the M18 parent and M18Ω (Table 3). None of the Spa antisera cross-reacted with purified recombinant M18 or purified recombinant Emm18, as determined by ELISA To confirm the presence of opsonic epitopes within the covalent structure of Spa, a peptide, S-Spa18(1–23)C, copying the N-terminal 23 amino acids of the purified 24 kDa fragment was chemically synthesized. The peptide was covalently linked to KLH and three rabbits were immunized with 100 μg doses using the same schedule described above. Anti-Spa, rabbit antiserum against the purified Streptococcal protective antigen, anti-S-Spa(1–23)C, rabbit antiserum against a synthetic peptide that copied the N-terminal 23 amino acids of Spa linked to KLH; anti-rM18, rabbit antiserum against intact, recombinant Type 18 M protein were used. Details of the assay are provided in Example 3. Experiments were repeated at least three times with similar results. Data presented are from one representative experiment. Briefly, serum from all three rabbits opsonized both the parent and M18Ω strains of group A Streptococci (Table 3), confirming the presence of opsonic epitopes within this limited region of Spa. The antiserum against the synthetic peptide of Spa was also used to identify the native protein in phage lysin extracts of M18Ω. The S-Spa18(1–23)C antiserum reacted with a single protein in the lysin extract with an apparent M.W. of 50 kDa (FIG. 3D), suggesting that the pepsin-derived Spa was a fragment of the larger native protein.

TABLE 3

Opsonization of Type 18 *Streptococci* by rabbit antisera against purified Spa and a synthetic peptide of Spa.

| | Percent neutrophils with associated *Streptococci*: | |
|---|---|---|
| Antiserum: | M18 | M18Ω |
| NRS | 4 | 6 |
| anti-Spa | 100 | 100 |
| anti-S-Spa(1–23)C | 72 | 100 |
| anti-rM18 | 96 | 16 |

The results of the opsonization assays were confirmed by indirect bactericidal tests as described in Example 3. Anti-rM18, rabbit antiserum against intact, recombinant Type 18 M protein; anti-crude pep M18, rabbit antiserum against a partially purified pepsin extract of whole Type 18 Streptococci; anti-Spa, rabbit antiserum against the purified Streptococcal protective antigen were used. The results provided in Table 4 show the Spa antiserum was bactericidal against both M18 and M18Ω while antiserum against rM18 was bactericidal against only the parent M18 strain and not against M18Ω.

TABLE 4

Bactericidal activity of rabbit antisera against rM18, a crude pepsin extract of Type 18 *Streptococci*, and purified Spa.

| | CFU surviving a 3 hour rotation | |
|---|---|---|
| Antiserum: | M18 Inoculum: 21 | M18Ω Inoculum: 32 |
| Normal Rabbit Serum | >10,000 | >10,000 |
| anti-rM18 | 460 | >10,000 |
| anti-crude pep M18 | 355 | 15 |
| anti-Spa | 230 | 0 |

Example 6

Opsonization of Heterologous Serotypes of Group A Streptococci by Spa Antiserum To determine whether Spa evoked opsonic antibodies against serotypes of group A Streptococci other than Type 18, opsonization assays were performed with antisera against purified Spa against the pep M18Ω and a series of selected Streptococci (Table 5). Both antisera opsonized Type 3 and Type 28 Streptococci, in addition to Type 18 organisms. Serotypes tested that were not opsonized by either antiserum were M1, M2, M5, M6, M13, M14, M19, and M24, all of which were from our laboratory collection. The anti-S-Spa18(1–23)C antisera did not opsonize Types 3 or 28 Streptococci, indicating that this limited region of Spa does not contain cross-opsonic epitopes.

TABLE 5

Opsonization of heterologous serotypes of group A *Streptococci* by rabbit antisera against purified Spa and a crude pepsin extract of M18Ω.

| | Percent neutrophilis with associated *Streptococci* in the presence of: | | | |
|---|---|---|---|---|
| Serotype (strain) | Preimmune | Anti-crude Pep M18Ω | Preimmune | Anti-Spa |
| M18 (282) | 0 | 100 | 6 | 100 |
| M3 (3375) | 14 | 88 | 8 | 56 |
| M28 (S2356) | 20 | 72 | 0 | 36 |

Example 7

Nucleic Acid and Amino Acid Sequence of a Cloned Fragment of the spa18 Gene

A fragment of the spa18 gene was cloned using PCR and degenerate inosine-containing oligonucleotide primers based on the N-terminal peptide sequence and the sequence of an internal peptide purified from a LysC digest of Spa. The forward set of primers derived from the N-terminal sequence of Spa from amino acid residues 7–11 contained the sequence GAR GTI GCI GAY CC (SEQ. ID NO: 6) The reverse primers, from the N-terminal sequence of the internal peptide, contained the sequences RTG IGA YTC RCT RTC (SEQ ID NO: 9) and RTG RCT YTC IGA RTC (SEQ. ID NO: 7). Nucleotide abbreviations are according to the UUPAC code for nucleic acids. PCR was performed as previously described using the chromosomal DNA from Type 18 Streptococci as the template. The forward primer in combination with the second reverse primer listed above resulted in a single PCR product of 336 bp, which was ligated into pCR2.1-TOPO (Invitrogen, Carlsbad, Calif.). DNA sequencing was performed by automated techniques in the University of Tennessee Molecular Resources Center using primers from the 5' and 3' flanking ends of the plasmid. The identity of the spa sequence was confirmed by comparing the translated DNA sequence to the amino acid sequence of Spa that was not used to construct the degenerate PCR primers.

The 336 bp PCR product and the translated amino acid sequence contained residues 12–23 of the sequence derived from the Spa protein (FIG. 4), confirming that the DNA was a fragment of spa18. A search of the current entries in GenBank® and the Type 1 Streptococcal genome sequence data base revealed that the spa18 gene fragment did not share sequence homology with any known proteins, suggesting that Spa is a new protective antigen of group A Streptococci.

Standard molecular biology techniques were used to obtain a full-length cDNA encoding a spa protein. The sequences for the full-length cDNA and encoded protein are depicted in FIGS. 5 and 6, respectively. The full-length protein includes a 37 residue signal peptide that is cleaved to form a mature spa polypeptide having the same N-terminus as the 23 residue peptide identified as SEQ ID NO:3.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A composition, comprising (a) a pharmaceutically acceptable carrier, binder, or diluent, and (b) an isolated polypeptide comprising the amino acid sequence set forth in SEQ ID NO:5.

2. The composition of claim 1 wherein the polypeptide consists of the amino acid sequence set forth in SEQ ID NO:5.

3. The composition of claim 1 further comprising an adjuvant.

4. The composition of claim 3 wherein the adjuvant is alum.

5. An isolated streptococcal protective antigen (Spa) polypeptide comprising the amino acid sequence set forth in SEQ ID NO:5.

6. An isolated streptococcal protective antigen (Spa) polypeptide consisting of the amino acid sequence set forth in SEQ ID NO:5.

7. An immunogen for protecting an animal against a group A streptococcal infection, comprising the isolated streptococcal protective antigen (Spa) polypeptide according to either claim 5 or claim 6.

* * * * *

SEQUENCE LISTING

```
<160> NUMBER OF SEQ ID NOS: 9

<210> SEQ ID NO 1
<211> LENGTH: 336
<212> TYPE: DNA
<213> ORGANISM: Streptococcus pyogenes
<220> FEATURE:
<221> NAME/KEY: misc_feature
<222> LOCATION: (1)...(336)
<223> OTHER INFORMATION: n = A,T,C or G

<400> SEQUENCE: 1
gaagtggcgg acccctctga tagtaagaaa cttattgagt taggtttggc taaatacctt        60
aatgataaat tacccttaa aactaaagaa gattcagaga ttttatcaga gttacgtgat        120
gtattaaaaa atgctaatcc agaaacatta aaaagtttac ttaatggtat ggatcaagga        180
catatatcat tttctgatag aaataatcgc tacaaccgtt tatctcaata tataaatagt        240
tttagaaaag atgatgatga ctatctacat aatggatatt ctttangaag tttagtgatt        300
```

```
gaagcaatta aataccgttt agatagcgaa tcccat                                336
```

```
<210> SEQ ID NO 2
<211> LENGTH: 112
<212> TYPE: PRT
<213> ORGANISM: Streptococcus pyogenes
<220> FEATURE:
<221> NAME/KEY: VARIANT
<222> LOCATION: (1)...(112)
<223> OTHER INFORMATION: Xaa = Any Amino Acid

<400> SEQUENCE: 2

Glu Val Ala Asp Pro Ser Asp Ser Lys Lys Leu Ile Glu Leu Gly Leu
 1               5                  10                  15

Ala Lys Tyr Leu Asn Asp Lys Leu Pro Phe Lys Thr Lys Glu Asp Ser
            20                  25                  30

Glu Ile Leu Ser Glu Leu Arg Asp Val Leu Lys Asn Ala Asn Pro Glu
        35                  40                  45

Thr Leu Lys Ser Leu Leu Asn Gly Met Asp Gln Gly His Ile Ser Phe
    50                  55                  60

Ser Asp Arg Asn Asn Arg Tyr Asn Arg Leu Ser Gln Tyr Ile Asn Ser
65                  70                  75                  80

Phe Arg Lys Asp Asp Asp Tyr Leu His Asn Gly Tyr Ser Leu Xaa
                85                  90                  95

Ser Leu Val Ile Glu Ala Ile Lys Tyr Arg Leu Asp Ser Glu Ser His
            100                 105                 110
```

```
<210> SEQ ID NO 3
<211> LENGTH: 23
<212> TYPE: PRT
<213> ORGANISM: Streptococcus pyogenes

<400> SEQUENCE: 3

Asp Ser Val Ser Gly Leu Glu Val Ala Asp Pro Ser Asp Ser Lys Lys
 1               5                  10                  15

Leu Ile Glu Leu Gly Leu Ala
            20
```

```
<210> SEQ ID NO 4
<211> LENGTH: 1872
<212> TYPE: DNA
<213> ORGANISM: Streptococcus pyogenes
<220> FEATURE:
<221> NAME/KEY: misc_feature
<222> LOCATION: (1)...(1872)
<223> OTHER INFORMATION: n = A,T,C or G

<400> SEQUENCE: 4
ataatataca ttctttctta ttaaataaaa ataacaatgt actacataaa gaagtttctg      60
ccattaaaat aaaagcacca tgagactata atagtatggt aaaacaaaaa agtatgccca     120
taacgggtag agaggaattg acatatgttt ttgagaaata aaaagcaaaa atttagcatc     180
agaaaactaa gtgctggtgc agcatcagta ttagttgcag caagtgtgtt gggaggggga     240
gtaagtgcgt atgcagattc agtaagtgga ttagaggtgg cagaccccta tgatagtaag     300
aaacttattg aattaggttt ggctaaatac cttaatgata aattacccct taaaactaaa     360
gaagattcag agattttatc agagttacgt gatgtattaa aaaatgctaa tccagaaaca     420
ttaaaaagtt tacttaatgg tatggatcaa ggacatatat cattttctga tagaaataat     480
cgctacaacc gtttatctca atatataaat agttttagaa aagatgatga tgactatcta     540
```

-continued

```
cataatggat attctttagg aagtttagtg attgaagcaa ttaaataccg tttagatagt    600
gagtcacatc taaaggaaga attacttaaa cagactgcag aacttgagca acgtaagaat    660
gcagaagttg atttaaaatc tgaaaaaaag agacttgaag cgcaaatana aaaagtagga    720
tatgatattg ctaataaaca gcaagaatta gaaaaagcgc gttcagatca aaaagagtta    780
agtgaatcta ttcaaaaatt aacgtcacga tttaaaaaag aaagtgatgc taaacaaaaa    840
gaactagatg aagctaaggc ggcaaataaa tctctttcag agtcagcaac aaaaacatta    900
gctagatcat ctaagataac taatgaatta aggataagt tggcggcttc agaaaaagat    960
aaaaatcgtg catttcaagt ttcttcagag ctagctaata agttgcatga acagaaact    1020
agtcgtgata aggctttagc agaatcaaaa gaattagcag ataaattggc agttaaaaca    1080
gcagaagctg aaaagttaat ggaaaacgtt ggtagtctag accgcttggt agagtctgca    1140
aaacgtgaaa tggctcaaaa attagcagaa attgaccaat taactgctga taaggctaag    1200
gctgatgcag agcttgcagc tgcaaatgac accattgcat cacttcaaac agagctagaa    1260
aaagttaaga cagagcttgc tgtttcagag cgcttgatcg aatcaggtaa acgtgaaatt    1320
gctgagcttg aaaaacaaaa agatgcttct gataaggctt tagcagaatc acaagctaat    1380
gtagcagagc ttgaaaaaca aaaagcagca tcagatgcta aggtagcaga gcttgaaaaa    1440
gaagttgaag ctgctaaagc tgaggttgca gatcttaaag cacaattagc taagaaagaa    1500
gaagagcttg aagccgttaa gaaagaaaaa gaagcgcttg aagctaagat tgaagagctc    1560
aaaaaagctc atgctgagga actttcaaaa cttaaagaaa tgcttgagaa gaagaccat    1620
gcgaatgcag atcttcaagc agaaatcaac cgcttgaagc aagagctagc tgacaggatt    1680
aagtcattgt cacaaggtgg tcgtgcttca caaacaaacc caggctctac aactgctaaa    1740
gcaggtcaat tgccatctac tggtgagtct gctaacccat tcttcactat tgcagctctt    1800
accgtcatcg ctggtgctgg tatggctgtg gtgtctccta aacgcaaaga aaactaagct    1860
ctttcctctt tc                                                        1872
```

<210> SEQ ID NO 5
<211> LENGTH: 570
<212> TYPE: PRT
<213> ORGANISM: Streptococcus pyogenes
<220> FEATURE:
<221> NAME/KEY: VARIANT
<222> LOCATION: (1)...(570)
<223> OTHER INFORMATION: Xaa = Any Amino Acid

<400> SEQUENCE: 5

```
Met Phe Leu Arg Asn Lys Lys Gln Lys Phe Ser Ile Arg Lys Leu Ser
  1               5                  10                  15

Ala Gly Ala Ala Ser Val Leu Val Ala Ala Ser Val Leu Gly Gly Gly
                 20                  25                  30

Val Ser Ala Tyr Ala Asp Ser Val Ser Gly Leu Glu Val Ala Asp Pro
             35                  40                  45

Ser Asp Ser Lys Lys Leu Ile Glu Leu Gly Leu Ala Lys Tyr Leu Asn
         50                  55                  60

Asp Lys Leu Pro Phe Lys Thr Lys Glu Asp Ser Glu Ile Leu Ser Glu
 65                  70                  75                  80

Leu Arg Asp Val Leu Lys Asn Ala Asn Pro Glu Thr Leu Lys Ser Leu
                 85                  90                  95

Leu Asn Gly Met Asp Gln Gly His Ile Ser Phe Ser Asp Arg Asn Asn
            100                 105                 110
```

-continued

Arg Tyr Asn Arg Leu Ser Gln Tyr Ile Asn Ser Phe Arg Lys Asp Asp
            115                 120                 125

Asp Asp Tyr Leu His Asn Gly Tyr Ser Leu Gly Ser Leu Val Ile Glu
        130                 135                 140

Ala Ile Lys Tyr Arg Leu Asp Ser Glu Ser His Leu Lys Glu Glu Leu
145                 150                 155                 160

Leu Lys Gln Thr Ala Glu Leu Glu Gln Arg Lys Asn Ala Glu Val Asp
                165                 170                 175

Leu Lys Ser Glu Lys Lys Arg Leu Glu Ala Gln Ile Xaa Lys Val Gly
            180                 185                 190

Tyr Asp Ile Ala Asn Lys Gln Gln Glu Leu Glu Lys Ala Arg Ser Asp
        195                 200                 205

Gln Lys Glu Leu Ser Glu Ser Ile Gln Lys Leu Thr Ser Arg Phe Lys
    210                 215                 220

Lys Glu Ser Asp Ala Lys Gln Lys Glu Leu Asp Glu Ala Lys Ala Ala
225                 230                 235                 240

Asn Lys Ser Leu Ser Glu Ser Ala Thr Lys Thr Leu Ala Arg Ser Ser
                245                 250                 255

Lys Ile Thr Asn Glu Leu Lys Asp Lys Leu Ala Ala Ser Glu Lys Asp
            260                 265                 270

Lys Asn Arg Ala Phe Gln Val Ser Ser Glu Leu Ala Asn Lys Leu His
        275                 280                 285

Glu Thr Glu Thr Ser Arg Asp Lys Ala Leu Ala Glu Ser Lys Glu Leu
    290                 295                 300

Ala Asp Lys Leu Ala Val Lys Thr Ala Glu Ala Glu Lys Leu Met Glu
305                 310                 315                 320

Asn Val Gly Ser Leu Asp Arg Leu Val Glu Ser Ala Lys Arg Glu Met
                325                 330                 335

Ala Gln Lys Leu Ala Glu Ile Asp Gln Leu Thr Ala Asp Lys Ala Lys
            340                 345                 350

Ala Asp Ala Glu Leu Ala Ala Ala Asn Asp Thr Ile Ala Ser Leu Gln
        355                 360                 365

Thr Glu Leu Glu Lys Val Lys Thr Glu Leu Ala Val Ser Glu Arg Leu
    370                 375                 380

Ile Glu Ser Gly Lys Arg Glu Ile Ala Glu Leu Glu Lys Gln Lys Asp
385                 390                 395                 400

Ala Ser Asp Lys Ala Leu Ala Glu Ser Gln Ala Asn Val Ala Glu Leu
                405                 410                 415

Glu Lys Gln Lys Ala Ala Ser Asp Ala Lys Val Ala Glu Leu Glu Lys
            420                 425                 430

Glu Val Glu Ala Ala Lys Ala Glu Val Ala Asp Leu Lys Ala Gln Leu
        435                 440                 445

Ala Lys Lys Glu Glu Leu Glu Ala Val Lys Lys Glu Lys Glu Ala
    450                 455                 460

Leu Glu Ala Lys Ile Glu Glu Leu Lys Lys Ala His Ala Glu Glu Leu
465                 470                 475                 480

Ser Lys Leu Lys Glu Met Leu Glu Lys Lys Asp His Ala Asn Ala Asp
                485                 490                 495

Leu Gln Ala Glu Ile Asn Arg Leu Lys Gln Glu Leu Ala Asp Arg Ile
            500                 505                 510

Lys Ser Leu Ser Gln Gly Gly Arg Ala Ser Gln Thr Asn Pro Gly Ser
        515                 520                 525

-continued

```
Thr Thr Ala Lys Ala Gly Gln Leu Pro Ser Thr Gly Glu Ser Ala Asn
    530                 535                 540

Pro Phe Phe Thr Ile Ala Ala Leu Thr Val Ile Ala Gly Ala Gly Met
545                 550                 555                 560

Ala Val Val Ser Pro Lys Arg Lys Glu Asn
                565                 570

<210> SEQ ID NO 6
<211> LENGTH: 14
<212> TYPE: DNA
<213> ORGANISM: Artificial Sequence
<220> FEATURE:
<223> OTHER INFORMATION: PCR primer
<220> FEATURE:
<221> NAME/KEY: modified_base
<222> LOCATION: (6)...(6)
<223> OTHER INFORMATION: n = inosine
<220> FEATURE:
<221> NAME/KEY: modified_base
<222> LOCATION: (9)...(9)
<223> OTHER INFORMATION: n = insosine

<400> SEQUENCE: 6
gargtngcng aycc                                                        14

<210> SEQ ID NO 7
<211> LENGTH: 15
<212> TYPE: DNA
<213> ORGANISM: Artificial Sequence
<220> FEATURE:
<223> OTHER INFORMATION: PCR primer
<220> FEATURE:
<221> NAME/KEY: modified_base
<222> LOCATION: (10)...(10)
<223> OTHER INFORMATION: n = insosine

<400> SEQUENCE: 7
rtgrctytcn gartc                                                       15

<210> SEQ ID NO 8
<211> LENGTH: 10
<212> TYPE: PRT
<213> ORGANISM: Streptococcus pyogenes

<400> SEQUENCE: 8

Tyr Arg Leu Asp Ser Glu Ser His Leu Lys
  1               5                  10

<210> SEQ ID NO 9
<211> LENGTH: 15
<212> TYPE: DNA
<213> ORGANISM: Artificial Sequence
<220> FEATURE:
<223> OTHER INFORMATION: PCR primer
<220> FEATURE:
<221> NAME/KEY: modified_base
<222> LOCATION: (4)...(4)
<223> OTHER INFORMATION: n = inosine

<400> SEQUENCE: 9
rtgngaytcr ctrtc                                                       15
```